United States Patent [19]

Musser et al.

[11] Patent Number: 6,030,835
[45] Date of Patent: Feb. 29, 2000

[54] METHODS AND COMPOSITION FOR IDENTIFYING GROUP A STREPTOCOCCUS

[75] Inventors: James M. Musser, Bellaire; Vivek Kapur, Houston, both of Tex.

[73] Assignee: Baylor College of Medicine, Houston, Tex.

[21] Appl. No.: 08/931,220

[22] Filed: Sep. 16, 1997

Related U.S. Application Data

[63] Continuation of application No. 08/306,542, Sep. 14, 1994, abandoned, and a continuation of application No. 08/160,965, Dec. 2, 1993.

[51] Int. Cl.[7] .............................. C12N 5/06; A61K 39/40; A61K 39/09; C12Q 1/00
[52] U.S. Cl. .................. 435/340; 424/165.1; 424/244.1; 435/4; 435/6; 435/7.34; 435/7.4; 435/7.92; 435/36; 435/253.4; 435/340
[58] Field of Search ................................... 435/4, 6, 7.34, 435/7.4, 7.92, 36, 253.4, 340; 424/165.1, 244.1

[56] References Cited

U.S. PATENT DOCUMENTS 4,454,121   6/1984   Beachy ..................................... 424/177

OTHER PUBLICATIONS

Kapur, V. et al. Microbial Pathogeneis 1993; 15: 327–346.
Poon–King, R. et al. Journal of Exp. Med. Aug. 1993; 178: 759–763.
Sevier, E. et al. Clin. Chem 1981; 27/11: 1797–1806.
Chavdrasekaran et al Leather Science 29:430–435 1982.
Linda He et al Journal of Clincal Microbiology 13:991–993, 1981.
Elliot Journ. of Exp. Med 81:573–592, 1945.
Audibert & Lise, *Immunol. Today* (1993) 14:281–284.
Beachy et al., *J. Exper. Med.* (1979) 150:862–877.
Becker et al., *Exp. Parasitol.* (1988) 67:268–280.
Bessen & Fischetti, In: Lasky L., ed. *Technological Advances in Vaccine Development*, Alan R. Liss. Inc. (publ.), pp. 493–502.
Björck et al., *Nature* (1989) 337:385–386.
Bunce et al., *Infect. & Immun.* (1992) 60:2636–2640.
Chappell & Stuart, *Vaccine* (1993) 11:643–648.
Dale et al, *J. Infect. Dis.* (1994) 169:319–323.
Elliott et al., *J. Exp. Med.* (1945) 81:573–592.
Fischetti et al., *Science* (1989) 244:1487–1490.
Gazzinelli et al., *Infect. Immun* (1990) 58:1437–1444.
Hauser & Schlievert, *J. Bacteriol.* (1990) 177:4536–4542.
Kapur et al., *Microb. Pathog.* (1993) 15:327–346.
Keene et al., *J. Exp. Med.* (1986) 163:536–549.
Keene et al., *Exp. Parasitol.* (1990) 71:199–206.
Kehoe, M., *Dept. of Microbio. Med. Sch. Univ. of Newcastle upon Tyne,* UK, *Vaccine (England)*, p. 797–806.
Lantz et al., *J. Bacteriol.* (1991) 173:495–504.
Murta et al., *Molec. & Biochem. Parasitol.* (1990) 43:27–38.
Musser et al., *Proc. Natl. Acad. Sci. USA* (1991) 88:2668–2672.
Musser et al., *J. Infect. Dis.* (1993) 167:337–346.
O'Connor et al., *J. Infect. Dis.* (1991) 163:109–116.
Otogoto & Kuramitsu, *Infect. & Immun.* (1993) 61:117–123.
Poirier et al., *J. Exper. Med.* (1988) 168:25–32.
Rotta et al., *J. Exp. Med.* (1988) 122:877–890.
Stjernquist–Desatnik et al., *Vaccine* (1990) 8:150–152.
Tai et al., *J. Biol. Chem.* (1976) 251:1955–1959.

*Primary Examiner*—James C. Housel
*Assistant Examiner*—Ja-Na N. Hines
*Attorney, Agent, or Firm*—Fulbright & Jaworski L.L.P.

[57] ABSTRACT

Methods and compositions are provided for identifying a group A Streptococcus in any of a variety of physiological samples, such as blood, saliva, throat swabs, cerebrospinal fluid, brocheolar lavage material, and biopsy material. The positions used include an extracellular cysteine protease or a fragment thereof, obtainable from *S. pyogenes* and containing at least one conserved epitope, or nucleic acid encoding the cysteine protease or fragment thereof. The compositions also find use in eliciting a protective immune response against a group A streptococcus infection.

12 Claims, 19 Drawing Sheets

CONTROL
PROTEASE-TREATED
Figure 6B

|  | SEQ. ID NO: | 998754 3170101 | 1111111111<br>22333334444466667788999999990000001111<br>24033337916788236361711224699127889158 8<br>29580253001034166598352499397343626102 |
|---|---|---|---|
|  |  |  | ** * * ** * * * * ** |
| speB1 | 20 | ACAGCAA | AGTGCCCCCGCCCCTCCCCAATACGACTACTACCAGGA |
| speB2 | 21 | ------- | G----------T---T---CG--------------- |
| speB3 | 22 | ------- | ------------T--------C--------------- |
| speB4 | 23 | ------- | ----T------T--------C--T------------- |
| speB5 | 24 | ------- | ------------T------------------------ |
| speB6 | 25 | ------- | ----------------T--C------------------ |
| speB7 | 26 | ------- | ----T---------T---CG---------T---- |
| speB8 | 27 | ------- | ----T------T--------C----------------- |
| speB9 | 28 | --G---- | ------------T--------C--------------- |
| speB10 | 29 | ------- | --C---------T--------C----C---------- |
| speB11 | 30 | --G-T-- | -------T-----------C-TT-------------- |
| speB12 | 31 | ---A--- | ---------A----------------------------- |
| speB13 | 32 | ------- | -----------T-G-----C---------------A- |
| speB14 | 33 | ------- | -------------------C------------------ |
| speB15 | 34 | ------- | -----------T--------CG------C------ |
| speB16 | 35 | ------- | -----------T-G-----C------------------ |
| speB17 | 36 | ------- | -------------------C--T-------------- |
| speB18 | 37 | --G-T-- | -------T----T------G-C-TT------------ |
| speB19 | 38 | ------- | ---TT-------T--------C-T---------T---- |
| speB20 | 39 | ------- | ----T-------T--T----C-----C-------C |
| speB21 | 40 | ------- | -----------T--------C--T-------------- |
| speB22 | 41 | ------- | -------------------CG---------------- |
| speB23 | 42 | --G---- | --------T---T--------C--G------------ |
| speB24 | 43 | -T----- | ----T--------T--T----CG-------------- |
| speB25 | 44 | G------ | ---A-T----------C-TT-----C-------- |
| speB26 | 45 | ------- | -----------T-G-----C-------T----G--- |
| speB27 | 46 | ------- | -------------------T------------------ |
| speB28 | 47 | -----G- | -----------T--------C------------------ |
| speB29 | 48 | ------- | -----------TT-------C-T--------------- |
| speB30 | 49 | ------- | ----T----------T----C------------------ |
| speB31 | 50 | --G---- | -------T---T-------C-T---------------- |
| speB32 | 51 | ------- | -----------TT-------C-TT-------------- |
| speB33 | 52 | ------- | -----------T---T----CG---------------- |
| speB34 | 53 | ------- | -----------TT-------CG--------C---A-- |
| speB35 | 54 | ------- | -------------------G----T-----T---- |
| speB36 | 55 | ------- | -----------T--TT----CG---------------- |
| speB37 | 56 | ------- | ----T-----T---T----C------------------ |
| speB38 | 57 | ------- | ------T-----T---T----CG--------------- |
| speB39 | 58 | ------- | -A-------------T----C----------------- |

METHODS AND COMPOSITION FOR IDENTIFYING GROUP A STREPTOCOCCUS

CROSS-REFERENCE TO RELATED APPLICATIONS

This application is a continuation of application Ser. No. 08/306,542, filed Sep. 14, 1994, now abandoned, a continuation-in-part of application Ser. No. 08/160,965 filed Dec. 2, 1993.

TECHNICAL FIELD

The present invention relates generally to the fields of molecular bacteriology and infectious disease. More specifically, the present invention relates to methods and compositions for identifying group A Streptococcus, particularly S. pyogenes.

BACKGROUND

Streptococcus pyogenes is a Gram-positive bacterium that is the etiological agent of several diseases in humans, including pharyngitis and/or tonsillitis, skin infections (impetigo, erysipelas, and other forms of pyoderma), acute rheumatic fever (ARF), scarlet fever (SF), poststreptococcal glomerulonephritis (PSGN), and a toxic-shock-like syndrome (TSLS). On a global basis, ARF is the most common cause of pediatric heart disease. For example, it is estimated that in India more than six million school-aged children suffer from rheumatic heart disease. In the United States, "sore throat" is the third most common reason for physician office visits and S. pyogenes is recovered from about 30% of children with this complaint. There are about 25–35 million cases of streptococcal pharyngitis per year in the United States, responsible for about 1–2 billion dollars per year in health care costs.

In recent years, an intercontinental increase in streptococcal disease frequency and severity has occurred for unknown reasons, although two variant pyrogenic exotoxin A (SPEA) molecules have been implicated. The amino acid residues characterizing the mutant SPEA molecules are located in an area of the toxin that, based on the recently published three-dimensional crystal structure of the related enterotoxin B from Staphylococcus aureus, form the T-cell receptor binding groove.

S. pyogenes synthesizes an extracellular zymogen of 371 amino acids (40,314 kDa) that can be transformed into an enzymatically active protease of 253 amino acids (27,588 kDa) by autocatalytic conversion. The zymogen contains one or more epitopes not associated with the truncated enzyme. Both the zymogen and active protease contain a single half-cysteine per molecule that is susceptible to sulfhydryl antagonists. In broth cultures, inactive precursor accumulates extracellularly during bacterial multiplication and reaches a maximum concentration at the end of logarithmic growth. Some strains yield up to 150 mg/liter of zymogen, and the molecule is a major extracellular protein. Thus, the streptococcal cysteine protease resembles many secreted bacterial extracellular protease virulence factors in having a specific signal peptide and a pro-sequence that is removed in an autocatalytic fashion to generate a fully active enzyme.

Detection of Group A Streptococcal infections has been hampered by the fact that currently available assays have relied upon detection of the Group A antigen. The extracellular protease, and antibodies generated against it, could also provide the basis of screening assays. Likewise, PCR-based assays could be used for detection of nucleic acid sequences which encode the extracellular protease. It therefore is of interest to identify conserved epitopes, particularly immunodominants conserved epitopes in the cysteine protease molecule, for the development of compositions and methods which can be used for screening for Group A Streptococcus organisms.

The continued great morbidity and mortality caused by S. pyogenes in developing nations, the significant health care financial burden attributable to Group A Streptococci in the United States, and increasing levels of antibiotic resistance in this pathogen highlight the need for a fuller understanding of the molecular pathogenesis of Streptococcal infection. Moreover, the recent disease increase underscores the lack of an efficacious vaccine, despite the repeated inclusion of *S. pyogenes* in lists of important human pathogens for which vaccines are needed.

Protection against systemic Streptococcal infection is thought to be due predominantly to type-specific opsonic anti-M protein IgG. As a consequence, immunoprophylaxis research has been conducted almost exclusively in the context of formulating an M protein vaccine. However, two major theoretical and practical problems have hindered this approach. First, more than 100 distinctive M protein types have been described based on serological and gene sequencing studies. The occurrence of this extensive array of serotypic variants means either that an effective M protein vaccine must be heterogenous in composition or that conserved protective M protein elements must be used. Formulation of a highly polyvalent vaccine has generated little enthusiasm, and a conserved pan-protective M protein fragment has yet to be identified. A second problem that has plagued M protein vaccine research is the observation that M proteins contain epitopes that cross-react with heart and other human tissue. This fact, in concert with the presumed autoimmune aspects of several Streptococcal diseases, has also slowed M protein vaccine development. It therefore would be of interest to develop an effective vaccine for the immune prophylactic prevention of Group A Streptococcal infection based upon other than the M protein and an efficient method of immunizing a human against Group A streptococcal infections.

Relevant Literature

Antibodies to molecules other than M proteins may provide protection against *S. pyogenes* infection as disclosed in the following references. Chappell and Stuart (*Vaccine* (1993) 11:643–8) found that intraperitoneal inoculation of washed bacterial cultures of an M-negative isolate protected mice against lethal challenge with *S. pyogenes* strains expressing M3, M18, or type 28 surface molecules. The non-type-specific immunity was attributed to the presence of antibodies against three proteins of $M_r$32, 43 and 46 kDa. Stjernquist-Desatnik et al. (*Vaccine* (1990) 8:150–2) showed that intranasal vaccination with heat-killed isolates of M negative strains of *S. pyogenes* protected against intranasal challenge with an isolate expressing serotype M50. Rotta et al. (*J. Exp. Med.* (1965) 122:877–90) demonstrated heterologous protective immunity in mice immunized via the intraperitoneal route with streptococcal cell wall preparations or material enriched in peptidoglycan, a Group A streptococcal cell wall component.

O'Connor and coworkers (*J. Infect. Dis.* (1991) 163:109–16) have suggested that neutralizing antibodies directed against the Streptococcal cell surface enzyme C5a peptidase may provide protection against Streptococcal colonization, but have not directly tested this hypothesis. A recent study by Dale et al. (*J. Infect. Dis.* (1994) 169:319–23) suggested that organisms pretreated with antibodies to the Group A Streptococcal surface molecule lipoteichoic acid (LTA) are significantly attenuated in a mouse model of infection. However, due to the lack of inclusion of a non-specific antibody control in that study, it is not possible to determine if the protective effect of the antibodies was due to interaction with LTA, or was due merely to the non-specific binding of immunoglobulin to the bacterial surface.

*S. pyogenes* culture supernatants contain a protease that has fibrinolytic activity. (Elliot (1945) *J. Exp. Med.* 81:573–92). The enzyme was purified, shown to be a cysteine protease (Liu et al. (1963) 238:251–6) and found to be identical to or an allelic variant of Streptococcal pyrogenic exotoxin B (SPE B). (Gerlach et al. (1983) *Zbl. Bakt. Hyg.* 255:221–3; Hauser and Schlievert (1990) *J. Bacteriol.* 172:4536–42).

SUMMARY OF THE INVENTION

Methods and compositions are provided for screening of physiological samples for prior exposure to *Streptococcus pyogenes* and as a means of monitoring disease status. The methods include the steps of contacting a sample with a reagent which specifically interacts with the SPE B gene, an expression product of the gene, or antibodies to the expression product, and detecting the resulting complex. The compositions include nucleic acid probes directed to a conserved region of the SPE B gene, a peptide comprising a sequence of at least 5 amino acids conserved amongst allelic variants of the SPE B gene, and antibodies to the peptide. Also provided are methods for preparation, isolation and/or purification of SPE B gene expression products and use of the products in cleaving or degrading extracellular matrix proteins, and as a vaccine against Group A Streptococcal infection either alone or in conjunction with a Streptococcal M-protein.

BRIEF DESCRIPTION OF THE DRAWINGS

The drawings are not necessarily to scale. Certain features of the invention may be exaggerated in scale or shown in schematic form in the interest of clarity and conciseness.

FIG. 2 shows the results of cleavage of human interleukin-1β (IL-1β) precursor by Streptococcal cysteine protease.

FIG. 11 shows alleles of speB. The polymorphic sites within the 160 bp upstream non-coding region and 1197 bp coding region of the speB gene are shown. The sequence described by Hauser and Schlievert (*J. Bacteriol* (1990) 1972:4536–42)) was arbitrarily designated as SpeB1, and the numbering of nucleotides and codons is cognate with that sequence. Only those nucleotides in the other alleles that differ from the speB1 sequence are shown. The position of each polymorphic nucleotide site is shown above the 39 alleles and is numbered in vertical format. Non-synonymous nucleotide changes are underlined and the positions of the coding changes are designated by an asterisk above of the coding region polymorphic sites. The seven polymorphic nucleotide sites in the upstream noncoding region are shown in the left of the figure, and the asterisk in speB6 denotes a deletion of an adenine residue. The codon (numbered in vertical format) containing the polymorphic nucleotide sites is shown below the 39 alleles. The DNA sequence data for speB2 - speB39 are available from EML/GenBank/DDBJ under accession numbers L26125-L26162. The DNA sequence data for speB1 was published in Hauser and Schlievert, *J. Bacteriol* (1990), 172:4536–42.

BRIEF DESCRIPTION OF THE INVENTION

Figure 1:
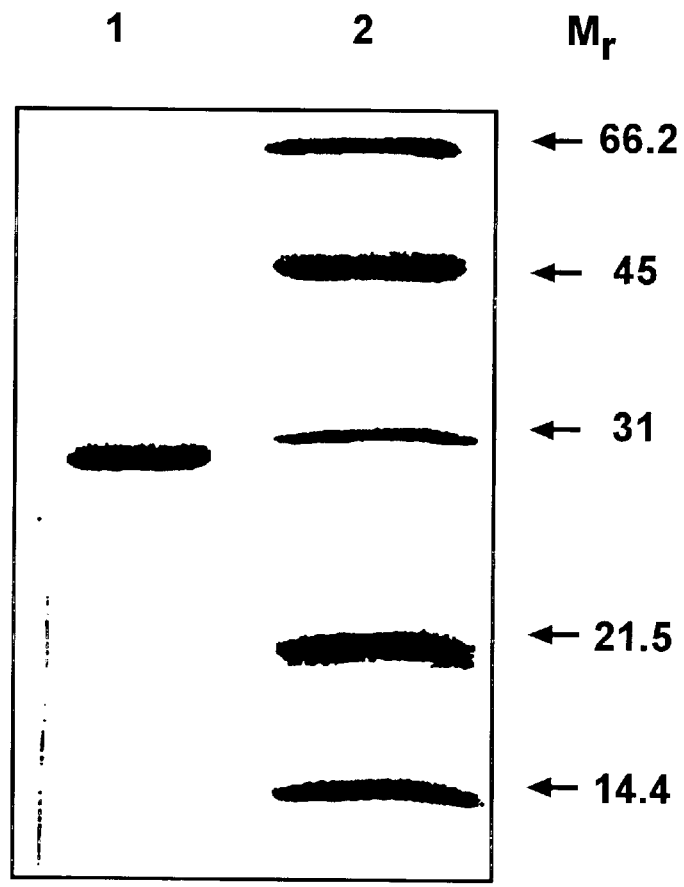
FIG. 1 shows the results of the purification of Streptococcal cysteine protease. Streptococcal cysteine protease was purified from strain MGAS 1719 using the method described in Example 2 and resolved by sodium dodecyl sulfate-polyacrylamide gel electrophoresis (SDS-PAGE). Lane 1:2 μg of the purified protease; lane 2: molecular weight standards.

Methods and compositions are provided for screening of host physiological samples such as blood, serum and plasma for evidence of infection of the host with *Streptococcus pyogenes* and for monitoring the disease status of the host. The host is any animal which is susceptible to infection with *S. pyogenes*, including humans. Evidence of infection includes detection of an *S. pyogenes* gene which encodes cysteine protease, detection of the cysteine protease or its zymogen, or antibodies to the cysteine protease or its zymogen. Currently available assays are not particularly sensitive as they rely upon detection of Group A specific antigen which may not be produced in sufficient quantities to be detected. In the current invention, the use of PCR-based assays with probes which detect amplified streptococcus nucleic acid encoding cysteine protease, or antibodies to SPEB, it is possible to overcome the sensitivity problem. Additionally, the use of peptides of the current invention provide for methods of identifying multiple strains when peptides including a conserved epitope, preferably an immunodominant conserved epitope, are used for either production of antibodies or for direct use. Examples of conserved epitopes include P(171) (SEQ ID NO:1) -V-I-E-K-V-K-P-G-E-Q-S-F-V-G-Q, Y(203) (SEQ ID NO:2) -H-N-Y-P-N-K-G-L-K-D-Y-T-Y-T-L, P(247) (SEQ ID NO:3) -T-Y-S-G-R-E-S-N-V-Q-K-M-A-I, I(344) (SEQ ID NO:4) -D-G-A-D-G-R-N-F-Y-H, and short stretches of at least 10 amino acids in the vicinity of 308–317, particularly immediately to the left of residue 308, or immediately to the right of residue 317.

When used as a vaccine, the cysteine protease may be any portion of the polypeptide that provokes an immune response, with consequent immunity, to Group A Streptococcal infections. Generally, the cysteine protease is obtainable as a translated portion of the speB gene, or fragments or derivatives thereof, which provoke an immune response. The cysteine protease can be naturally occurring, or partially or wholly synthetic. A mammal can be immunized against Group A Streptococcal infection by administration of the vaccine to the mammal in an amount sufficient to confer immunity to Group A Streptococcal infection. Diseases for which immunity is desireable include: phyaryngitis, tonsillitis, skin infections, scarlet fever, sepsis, erysipelis, fasciitis, pneumonia, acute rheumatic fever, poststreptococcal glomerulonephritis, cellulitis, bacteremia, and meningitis.

A vaccine based upon the speB gene product offers several advantages over those which are M-protein based. For example, antibodies to M-proteins are known to cross react with various host tissues, and there is considerable concern that an M-protein vaccine may evoke human autoimmune-mediated disease due to this sharing of epitopes. The greater than 100 identified M protein types elicit a predominantly type-specific immunity. Thus, an effective M-protein based vaccine would need to be highly polyvalent or directed against as yet unidentified conserved pan-protective M-protein epitopes. The vaccine of the present invention is not type-specific and therefore is useful in the prevention of any Group A Streptococcal infections. Antibodies to the cysteine protease or its zymogen are not known to cross-react with host tissues.

*Streptococcus pyogenes* is a gram positive coccus which is β-hemolytic, expresses group A antigen and is susceptible to bacitracin. For the purpose of this disclosure, a microorganism is considered to be the same as or equivalent to *Streptococcus pyogenes* if in its genome is a coding sequence for an extracellular protease which is involved in the pathogenesis of the microorganism. Accordingly, peptides are provided which immunologically mimic extracellular proteases encoded by the *S. pyogenes* bacterium, particularly proteins encoded by the speB region of the bacterial genome. To accommodate strain-to-strain variations among different isolates, adjustments for conservative substitutions and selection among the alternatives where non-conservative substitutions are involved, may be made. These peptides can be used individually or together for detection of the bacterium or of antibodies to the bacteria in a physiological sample. Depending upon the nature of the test protocol, the macromolecules may be labeled or unlabeled, bound to a solid surface, conjugated to a carrier as other compounds, or the like.

Of particular interest are peptides which are derived from the protein encoded by the speB gene, which encodes a zymogen and extracellular cysteine protease that cleaves human interleukin 1β precursor to form biologically active IL-1β, a major cytokine mediating inflammation and shock. The purified protease cleaves fibronectin and rapidly degrades vitronectin. The protein has no substantial activity against laminin. The cysteine protease also cleaves fibronectin from human umbilical vein endothelial cells grown in vitro. Other organisms which produce extracellular proteases which are involved in pathogensis of the host organism may also be used as a source of the enzyme or fragments thereof, and of genetic material for use in the subject invention.

Several human pathogenic bacteria express extracellular proteases capable of degrading ECM proteins. Among these organisms are *Pseudomonas aeruginosa,* (Morihara Kamp Homma, In: Holder IA, ed. Bacterial enzymes and virulence, FL CRC Press, 1985; 41–75) and *Porphyromonas (Bacteriodes) gingivalis,* (Lantz et al, J. Bacteriol 1991; 173:495–504; and Otogoto and Kuramitsu, Infect Immun 1993; 61:117–23) two bacterial species that produce host tissue destruction by degradation of collagen and fibronectin, respectively. It is also noteworthy that *Trypanosoma cruzi,* the parasitic flagellate which causes American trypanosomiasis (Chagas' disease), expresses a cell-surface cysteine protease that is a major antigen in humans, (Gazzinelli et al, Infect Immun 1990; 58:1437–44; and Murta ACM et al, Molec Biochem Parasitol 1990; 43:27–38) and is thought to be an important virulence factor. (Eakin AE et al, J Biol Chem 1992; 267: 7411–20). The enzyme (cruzipain) cleaves immunoglobulin G molecules and hydrolyzes the Fc fragment, (Murta ACM et al, Molec Biochem Parasitol 1990; 43:27–38) thereby assisting the organism to evade the immunological consequences of antibody binding. *Entamoeba histolytica,* the cause of amebiasis, also produces an extracellular cysteine protease that is widely believed to be a major virulence factor. (Keene WE et al, J Exp Med 1986; 163:536–49.) Like the streptococcal cysteine protease, the *E. histolytica* enzyme degrades several ECM proteins, including type I collagen, fibronectin, and laminin. (Keene WE et al, J Exp Med 1986; 163:536–49.) The protease also causes cytopathic effect on cell culture monolayers, (Keene WE et al, Exp Parasitol 1990; 71: 199–206) and is involved with production of tissue necrosis in rat models of acute amebiasis. (Becker I et al, Exp Parasitol 1988; 67:268–80.)

The peptide will include at least five, sometimes six, sometimes eight, sometimes about 22 amino acids, but usually fewer than 50 amino acids, preferably fewer than about 25 amino acids included within the region 1197 bp of the coding region of the cysteine protease gene. The peptide includes at least one linear epitope within the amino acid sequence which corresponds to the preproenzyme, the entire sequence of which is as follows:

which the above-cited peptide sequence corresponds may exhibit strain-to-strain variation.

It should be understood that the polypeptides employed in the subject invention need not be identical to a cysteine protease obtainable from *S. pyogenes,* so long as the subject compounds are able to provide for immunological interaction with a cysteine protease obtainable from at least one of the strains of *S. pyogenes.* Therefore, the subject polypeptides may be subject to various changes such as insertions, deletions, and substitutions, other conservative or non-conservative, where such changes might provide for certain advantages in their use. By conservative substitution is intended combinations such as gly, ala; val, ile, leu; asp, glu; asn, gln; ses, thr; lys, arg; and phe tyr. Usually, the sequence will not differ by more than 20% from the sequence of at least one strain of *S. pyogenes* except where additional amino acids may added at either terminus for the purpose of providing an "arm" by which the peptides of this invention may be immobilized conveniently. The arms usually will be at least 5 amino acids, and may be 50 or more amino acids.

Of particular interest as immunogens are peptides of at least 10 amino acids which include one or more of the following: amino acids 308–317, amino acids immediately adjacent to and to the left of residue 308, and amino acids immediately adjacent to and to the right of residue 317 of *S. pyogenes* cysteine protease.

The peptides can be prepared in a wide variety of ways. The cysteine protease itself can be purified from natural sources, for example by binding to Red A, or by other means known to those skilled in the art of protein purification, such as affinity chromatography using antibody to the protein. The peptides, because of their relatively short size, also may be synthesized in solution or on a solid support in accordance with conventional techniques. Various automatic synthesizers are commercially available and can be used in accordance with known protocols. The peptides are selected based upon the location of allelic variation and conservation and the cysteine protease antigenic index generated with a Jameson-Wolf plot. For example, peptides corresponding to

| 10 | 20 | 30 | 40 | 50 | 60 | |
|---|---|---|---|---|---|---|
| MNKKKLGIRL | LSLLALGGFV | LANPVFADQN | FARNEKEAKD | SAITFIQKSA | AIKAGARSAE | 60 |
| DIKLDKVNLG | GELSGSNMYV | YNISTGGFVI | VSGDKRSPEI | LGYSTSGSFD | ANGKENIASF | 120 |
| MESYVEQIKE | NKKLDTTYAG | TAEIKQPVVK | SLLDSKGIHY | NQGNPYNLLT | PVIEKVKPGE | 180 |
| QSFVGQHAAT | GCVATATAQI | MKYHNYPNKG | LKDYTYTLSS | NNPYFNHPKN | LFAAISTRQY | 240 |
| NWNNILPTYS | GRESNVQKMA | ISELMADVGI | SVDMDYGPSS | GSAGSSRVQR | ALKENFGYNQ | 300 |
| 310 | 320 | 330 | 340 | 350 | 360 | |
| SVHQINRSDF | SKQDWEAQID | KELSQNQPVY | YQGVGKVGGH | AFVIDGADGR | NFYHVNWGWG | 360 |
| GVSDGFFRLD | ALNPSALGTG | GGAGGFNGYQ | SAVVGIKP. | 399 | | |

The peptide will be as small as possible while still maintaining substantially all of the sensitivity of the larger peptide, the sequence of which is shown above. In some cases there may be two or more smaller not overlapping peptides, each contained within the parent peptide, which separately or together provide equivalent sensitivity to the parent peptide. The peptide sequences may be modified by terminal-$NH_2$ acylation, terminal carboxy amidation, for example, ammonia methylamine, etc. Furthermore, it will be appreciated that the amino acid sequence need not correspond exactly to any portion of the sequence given above, provided that the relevant epitope(s) are substantially retained. It also will be appreciated that the base pairs to the variable region (amino acids 308–317) of mature Streptococcal cysteine protease are prepared. Subsequently, peptides which correspond to the invariant calculated antigenic peaks in the cysteine protease are used for immunization. Examples of such sequences include P(171) (SEQ ID NO:1) -V-I-E-K-V-K-P-G-E-Q-S-F-V-G-Q, Y(203) (SEQ ID NO:2) -H-N-Y-P-N-K-G-L-K-D-Y-T-Y-T-L, P(247) (SEQ ID NO:3) -T-Y-S-G-R-E-S-N-V-Q-K-M-A-I, I(344) (SEQ ID NO:4) -D-G-A-D-G-R-N-F-Y-H. Naturally occurring variant zymogens of cysteine protease and cysteine protease itself display unique liner B-epitopes.

To prepare synthetic peptides, overlapping 10-mer peptides are used which overlap 2 amino acid residues with the previous 10-mer in a consecutive primary sequence corresponding to the 371 amino acids of the mature cysteine protease zymogen (translated product minus leader sequence). Synthetic 10-mers corresponding to each variant amino acid residue are also used. The variant amino acids are positioned in the middle of the 10-mer.

Once the 10-mer peptides are synthesized, an ELISA is used to examine the reactivity of each peptide using a panel of monoclonal antibodies raised against purified cysteine protease as well as sera obtained from patients with symptoms of S. pyogenes infection. The linear B cell epitopes are then determined; the same linear B cell epitopes will most likely be recognized by all of the sera from patients with S. pyogenes* infection.

Both site-directed and random mutagenesis schemes can be employed to identify residues that disrupt cysteine protease function and zymogen processing, and to map regions that constitute antigenic domains of the protein. FIG. 8 shows the processing sites, locations of amino acid variations found in the proteins made by the speB2 and speB4 alleles, and amino acids that are targets for mutation. Targets for functional amino acid replacement are based on biochemical analysis of cysteine protease (Tai, et al., *J. Biol Chem.* (1976) 251:1955–91) and by analogy with similar residues in the eukaryotic cysteine protease.

To create a stable zymogen to facilitate crystallographic studies and generate enzymatically deficient or inactive protease for structure-function studies, mutant forms of the cysteine protease protein are made and characterized. A targeted mutagenesis scheme creates changes that: (i) disrupt protease activity; (ii) prevent zymogen processing; (iii) prevent substrate binding; and (iv) alter immunoreactivity. Amino acids are changed to structurally neutral alanine. As an example, a mutant protein that lacks protease activity, but which retains antigenicity, can be generated by mutagenesis of the single cysteine residue (Cys-192→Ala-192) at the catalytic site of the molecule. Also, His-340 and Gn-185 and Asn-356 are mutagenized. These three changes are epistatic to the Cys-192 mutation, but may alone exhibit altered activity. Trp-357, thought to be involved in substrate binding and similarly positioned within papain, is also to be targeted.

A stable zymogen precursor is also created by mutating residues surrounding the protease cleavage site at Lys-145. In addition, mutagenesis of Cys-192 may prevent autoproteolysis, as occurred for a Cys→Ser mutant of papain, the prototype cysteine protease. Other mutagenesis targets include a putative nucleotide binding domain (GVGKVG) (SEQ ID NO:6) and a potential collagen docking region [$(GXX)_3$] within the carboxy terminal portion of the protein. Site-directed mutagenesis is used, by the charged-to-alanine-scanning method, to substitute positively and negatively charged amino acids (often involved in recognition and activity) with alanine. Many of the charged residues (14 lysine, 7 arginine, 12 aspartate, and 7 glutamate residues in the mature peptide) are expected to lie on the surface of the cysteine protease structure, and some are expected to define epitopes on the molecule. In particular, a region of charged amino acids, from 307 to 321 (8/15 charged), is examined; this region includes the site of speB2 and speB4 amino acid substitutions. Residues in antigenic regions identified in the epitope mapping studies are also mutated.

In order to create mutant speB proteins, as an example, first, the speB gene is amplified from a *S. pyogenes* strain, with PCR, and the product is cloned into a multicopy filamid vector such as pBluescript (Stratagene, La Jolla, Calif.). This vector is chosen because it carries the regulated lac promoter and can be replicated as a single-stranded molecule for site-directed mutagenesis. Cloning is designed to place the promoter, ribosome binding site and speB reading frame 3' to an inducible promoter, such a lac promoter, on the vector so that the protein can be conditionally over-expressed in a bacterial host such as an inducer of the inducible promoter is added to the culture broth. For example, with the lac promoter, the *E. coli* when the lac inducer, 1PTG, can be added. The speB promoter is included requiring expression in *S. pyogenes.* Whole cell extracts and periplasmic shockates of *E. coli* cells carrying this primary speB clone are examined for the presence of the cysteine protease protein by SDS-PAGE and by Western blotting with anti-cysteine protease antibody. The resulting plasmid is the target for mutagenesis.

Oligonucleotide-directed mutations, such as substitutions, deletions and small insertions, are created on uracil-containing single-stranded templates by the method of Kunkel (Kunkel, 1985). When possible, mutagenic primers are designed to incorporate a unique restriction site into the speB gene for mapping and mutant selection. Both single and multiple alanine substitutions are created at the residues indicated above. Once residues critical to function are identified, small regions surrounding them are deleted or substituted, by using the same methods, to further characterize the region and to preclude reversion. When crystallographic data is available, additional amino acids are mutated.

A random mutagenesis scheme also can be employed. Variant proteins created by this method are most useful for epitope screening, although molecules with altered kinetics and substrate recognition also may be recovered. Regions of the speB sequence are randomized with mixed oligonucleotides in the primed-mutagenesis protocol, or short, in-frame deletions within the gene are created with a modification of the DNAse 1-linker insertion/deletion protocol of Palzkill and Bostein (Palzkill and Bostein, 1991).

To identify protease minus mutations, bacterial host cells producing potential mutant proteins are first screened for protease activity on casein agar plates. Since secretion of cysteine protease to the periplasm is expected, protease activity can be observed on plates. If this screening strategy is successful, thousands of colonies are rapidly examined for functional mutations in cysteine protease. If cysteine protease must be completely secreted from *E. coli* to exhibit activity, then osmotic shockates of each presumptive mutant strain are assayed for protease activity.

Alternatively, hybrid-DNA technology may be employed where a synthetic gene may be prepared by employing single strands which code for the polypeptide or substantially complementary strands thereof, where the single strands overlap and can be brought together in an annealing medium so as to hybridize. The hybridized strands may then be ligated to form the complete gene and by choice of appropriate termini, the gene may be inserted into an expression vectors. Alternatively, the region of the bacterial genome coding for the peptide may be cloned by conventional recombinant DNA techniques and expressed.

An example of a DNA coding sequence which may be used for expressing the cysteine protease is as follows (SEQ ID NO:7):

```
                10          20          30          40          50
atg aat aaa aag aaa tta ggt atc aga tta tta agt ctt tta gca tta ggt gga    54
ttt gtt ctt gct aac cca gta ttt gcc gat caa aac ttt gct cgt aac gaa aaa   108
gaa gca aaa gat agc gct atc aca ttt atc caa aaa tca gca gct atc aaa gca   162
ggt gca cga agc gca gaa gat att aag ctt gac aaa gtt aac tta ggt gga gaa   216
ctt tct ggc tct aat atg tat gtt tac aat att tct act gga gga ttt gtt atc   270
gtt tca gga gat aaa cgt tct cca gaa att cta gga tac tct acc agc gga tca   324
ttt gac gct aac ggt aaa gaa aac att gct tcc ttc atg gaa agt tat gtc gaa   378
caa atc aaa gaa aac aaa aaa tta gac act act tat gct ggt acc gct gag att   432
aaa caa cca gtt gtt aaa tct ctc ctt gat tca aaa ggc att cat tac aac caa   486
ggt aac cct tac aac cta ttg aca cct gtt att gaa aaa gta aaa cca ggt gaa   540
caa tct ttt gta ggt caa cat gca gct aca gga tgt gtt gct act gca act gct   594
caa att atg aaa tat cat aat tac cct aac aaa ggg ttg aaa gac tac act tag   648
aca cta agc tca aat aac cca tat ttc aac cat cct aag aac ttg ttt gca gct   702
atc tct act aga caa tac aac tgg aac aac atc cta cct act tat agc gga aga   756
gaa tct aac gtt caa aaa atg gcg att tca gaa ttg atg gct gat gtt ggt att   810
tca gta gac atg gat tat ggt cca tct agt ggt tct gca ggt agc tct cgt gtt   864
caa aga gcc ttg aaa gaa aac ttt ggc tac aac caa tct gtt cac caa att aac   918
cgt agc gac ttt agc aaa caa gat tgg gaa gca caa att gac aaa gaa tta tct   972
caa aac caa cca gta tac tac caa ggt gtc ggt aaa gta ggc gga cat gcc ttt  1026
gtt atc gat ggt gct gac gga cgt aac ttc tac cat gtt aac tgg ggt tgg ggt  1080
gga gtc tct gac ggc ttc ttc cgt ctt gac gca cta aac cct tca gct ctt ggt  1134
act ggt ggc ggc gca ggc ggc ttc aac ggt tac caa agt gct gtt gta ggc act  1188
aaa cct tag 1197
```

Fragments from this sequence may be employed for expression of peptide fragments, conservative base changes can be made, where the modified codon (s) code for the same amino acid(s), or non-conservative changes in the coding sequence may be made, where the resulting amino acid may be a conservative or non-conservative change.

The coding sequence may be extended at either the 5'- or a 3'-terminus or both termini to extend the peptide while retaining its epitopic site. The extension may provide for an arm for linking, as a label, for example an enzyme, for joining two or all of the peptides together in the same chain, for providing antigenic activity, and the like.

For expression, the coding sequence will be provided with start and stop codons, promoter and terminator regions, and usually a replication system to provide an expression vector for expression in a cellular host, for example prokaryotic or eukaryotic, bacterial, yeast, and mammalian, etc.

The sequences by themselves, fragments thereof, or larger sequences, usually at least 15 bases, preferably at least 18 bases, may be used as probes for detection of bacterial DNA. Numerous techniques are described, such as the Southern technique, Northern technique, and improvements thereon, as well as other methodology.

Conveniently, the polypeptides may be prepared as fused proteins, where the polypeptide may be the N- or C-terminus of the fused polypeptide. The resulting fused protein can be used directly by itself as the reagent or the subject peptide may be cleaved from all or a portion of the remaining sequence of the fused protein. With a polypeptide where there are no internal methionines, by introducing a methionine at the fusion site, the polypeptide may be cleaved employing cyanogen bromide. Where there is an internal methionine, it will be necessary to provide for a proteolytic cleavage site, for example, poly-lysine, or -arginine, or combinations thereof. A wide variety of proteases, including dipeptidases, are well known and the appropriate processing signal can be introduced at the proper site. The processing signal may have tandem repeats so as to insure cleavage, since the presence of one or more extraneous amino acids will not interfere with the utility of the subject polypeptides.

The subject peptides may be employed linked to a soluble macromolecular (≧20 kd) carrier. Conveniently, the carrier may be a poly (amino acid) either naturally occurring or synthetic, to which antibodies are unlikely to be encountered in human serum. Illustrative polypeptides include poly-L-lysine, bovine serum albumin, keyhole limpet hemocyanin, bovine gammaglobulin, etc. The choice is primarily one of convenience and availability. With such conjugates, there will be at least one molecule of at least one subject peptide per macromolecule, and not more than about one per 0.5 kd, usually not more than one per 2 kd of the macromolecule. One or more different peptides may be linked to the same macromolecule.

The manner of linking is conventional, employing such reagents as p-maleimidobenzioc acid, p-methyldithiobenzioc acid, maleic acid anhydride, succinic acid, anhydride, glutaraldehyde, etc. The linkage may occur at the N-terminus, C-terminus, or at a site intermediate the ends of the molecule. The subject peptide may be derivatized for linking, may be linked while bound to a support, or the like.

The compounds may be employed as labeled or unlabeled compounds, depending upon their use. By label is intended a molecule which provides, directly or indirectly, a detectible signal. Various labels may be employed, such as radionucleides, enzymes, fluorescers, chemiluminescers, enzyme substrates, cofactors or inhibitors, particles, e.g., magnetic particles or the like. In addition, the polypeptides may be modified in a variety of ways for binding to a surface, e.g., microtiter plate, glass beads, chromatographic surface, e.g., paper, cellulose, silica gel, and the like. The particular manner in which the polypeptides are joined to another compound or surface is conventional and finds example and illustration in the literature.

Various assay protocols may be employed for detecting the presence of either antibodies to the cysteine protease or the cysteine protease itself, to the zymogen or antibodies to the zymogen. Of particular interest is using the peptide as the labeled reagent, where the label allows for a detectable signal, or binding the peptide, either directly or indirectly to a surface, where antibody to the peptide in the sample will become bound to the peptide on the surface. The presence of human antibody bound to the peptide then can be detected by employing xenogeneic antibody specific for human immunoglobulin, normally both human IgM and IgG or a labeled protein specific for immune complexes, for example, Rf factor or *S. aureus* protein A. Various heterogenous protocols may be employed, either competitive or non-competitive. The peptide may be bound to a surface or support and labeled antibody allowed to compete with antibody in the sample for the limited amount of bound peptide. The amount of label bound to the support would be related to the competitive antibody in the sample. Antibody can be bound to the support in the sample combined with labeled peptide. After contact of the reaction mixture with the bound antibody, the amount of label bound to the support relates to the amount of antibody in the sample.

Xenogeneic anti-human antibody, e.g., antibodies to the $F_c$ region of IgG and IgM immunoglobulins can be bound to a support. The sample is contacted with the immunoglobulins and labeled peptide, whereby the amount of labeled peptide bound to the support is indicative of the presence of the cognate antibodies. Alternatively, homogeneous assays can be employed where the peptide is bound to an enzyme, fluorescence, or other label, where the binding of antibody to the peptide provides the ability to discriminate between the label involved with a specific binding pair complex, and label which is not involved in the complex. Assays involving such techniques are described in the literature.

As an illustration of the subject invention, the subject peptides may be conjugated to a fluorescent molecule, such as fluorescein, rhodamine, or umbelliferone. Various techniques might be used for detecting complex formation with antibodies, e.g, fluorescence polarization. In this assay, the florescence polarization is different between complexed and uncomplexed peptide conjugate. Apparatuses are available for measuring changes in fluorescence polarization.

Illustrative of an assay technique is the use of sample containers, e.g., a microtiter plate wells, where the subject polypeptide or conjugates thereof adhere to the container bottom and/or walls either covalently or noncovalently. The sample, normally human blood or serum diluted in an appropriately buffered medium, is added to the container and a sufficient time allowed for complex formation between the polypeptide(s) and any antibodies in the sample. The supernatant is removed and the container washed to remove non-specifically bound proteins.

A labeled specific binding protein which specifically binds to the complex is employed for detection. To the container may be added xenogeneic antisera to human immunoglobulin, particularly anti-(human IgM and IgG) in appropriately buffered medium. The xenogeneic antisera normally are labeled with a detectible label, for example, radionucleide or enzyme. Instead of antisera, a protein specific for the immune complex can be employed, e.g., *S. aureus* protein A. The label then may be detected. For example, with an enzyme, after removal of a non-specifically bound enzyme label, a developer solution is added. The developer solution will contain an enzyme substrate and possible enzyme cofactors, chromogens, etc. which upon reaction provide a colored or fluorescent product which can be detected calorimetrically or fluorometrically, respectively.

Antibodies to the peptides of the subject invention can be prepared in conventional ways. Both polyclonal and monoclonal antibodies can be prepared, depending upon the intended purpose; hybridoma technology can be used for preparation and isolation of monoclonal antibodies which bind to specific epitopes on the cysteine protease, its derivatives, mutations, and the like.

Depending upon the nature of the assay, the physiological sample, for example saliva, blood, plasma, cerebrospinal fluid, throat swabs, bronchoalvealar lavage material, biopsy material, or serum, may be pretreated by dilution into an assay medium, which usually will be an aqueous buffered medium employing one of a variety of buffers such as phosphate, tris, or the like. Bacterial culture both or other culture medium can also be assayed for the presence of organisms, and/or to identify an organism. Usually the pH will be in the range of 6–8. The sample then will be combined with a reagent in accordance with the appropriate protocol and sufficient time allowed for binding. Where a heterogeneous system is used, usually the stages will be followed by washes, to minimize non-specific binding. At the end of the procedure, the label will be detected in accordance with conventional ways.

The physiological sample generally will be human, although veterinary applications are also of interest, particularly mouse and mink, or other animals susceptible to infection by Group A Streptococci.

Besides the use of the subject macromolecules and their analogs in assays, the subject peptides may also find use by themselves or in combination to generate a protective immune response, and in vaccines, particularly for humans, but also in commercially valuable animals such as mink which are susceptible to Group A Streptococci infection, or other animals such as mice. The peptides may be formulated in a convenient manner, generally at concentrations in the range of 1 μg to 20 mg-kg. Physiologically acceptable media may be used as carriers, such as sterile water, saline, phosphate buffered saline, and the like. Adjuvants may be employed, such as aluminum hydroxide gel, and the like. Administration may be by injection, for example intramuscularly, intraperitoneally, subcutaneously, intravenously, etc. Administration may be one or a plurality of times, usually at one to four week intervals. In addition, the efficacy of the vaccine may be enhanced by the addition of a Streptococcal M protein antigen. In this vaccine, the conserved domain of the Streptococcal M protein is combined with the cysteine protease. Preferably, the M protein that is used does not cross-react immunologically with host tissues. Production of antibodies may be used as a protection against group A Streptococcus, where protection may delay onset of death or prevent mortality due to infection.

Purified cysteine protease has several uses including use as a replacement for trypsin or other proteases in obtaining isolated cells, particularly those which are within a protein matrix, e.g., a collagen matrix, such as biopsy specimen, or adhered to a tissue culture plate or petri dish, or bound to an affinity column via a protein arm. The protease also finds use in the removal of excess scar tissue.

The DNA encoding the peptides of the subject invention find use as probes for identifying other sources of cysteine protease, and in PCR-based assays for identifying the presence of a group A Streptococcus, particularly *S. pyogenes* in a physiological sample.

The following examples are given for the purpose of illustrating various embodiments of the methods of the present invention and are not meant to limit the present invention in any fashion.

EXAMPLE 1

Bacterial Isolates

Table 1 shows the 68 strains of *S. pyogenes* studied. MGAS 1719 is identical to strain B220, the designation assigned by Dr. R. Lancefield to strain 5797. The strain expresses type 8 T antigen but is serologically nontypeable for M protein.

TABLE 1

Properties of 68 S. pyogenes strains representing 50 ETs[a]

| ET | Serotype[b] | MGAS no.[c] | Disease or site[d] | Country and year | speB allele | opacity factor phenotype | M protein class |
|---|---|---|---|---|---|---|---|
| 1 | M1 | 19 | pharyngitis | USA - 1980s | speB2 | − | I |
|  | M1 | 166 | TSLS | USA - 1980s | speB2 |  |  |
|  | M1 | 285 | SID | USA - 1980s | speB2 |  |  |
|  | M1 | 326 | TSLS | USA - 1980s | speB2 |  |  |
|  | M1 | 480 | invasive | Yugoslavia - 1990s | speB2 |  |  |
|  | M1 | 579 | cellulitis | Canada - 1980s | speB2 |  |  |
|  | M1 | 1253 | scarlet fever | UK - 1920s | speB2 |  |  |
| 2 | M3 | 75 | pharyngitis | USA - 1980s | speB3 | − | I |
|  | M3 | 157 | TSLS | USA - 1980s | speB3 |  |  |
|  | M3 | 315 | TSLS | USA - 1980s | speB3 |  |  |
|  | M3 | 1251 | scarlet fever | USA - 1920s | speB3 |  |  |
| 34 | M14 | 660 | unknown | Egypt - 1971 | speB8 | − | I |
| 35 | M46 | 1222 | ARF | USA - 1953 | speB2 | − | I |
| 36 | M76 | 1832 | unknown | unknown | speB33 | + |  |
| 21 | M12 | 282 | SID | USA - 1980s | speB1 | − | I |
| 37 | M1 | 789 | NP | USA - 1946 | speB5 | − | I |
| 38 | M41 | 1841 | unknown | unknown | speB29 | − | I |
| 39 | M33 | 807 | blood | USA - 1969 | speB15 | − | I |
| 40 | PT5757 | 1871 | unknown | unknown | speB34 |  |  |
| 40 | PT4854 | 1893 | unknown | unknown | speB3 |  |  |
| 42 | M8 | 429 | unknown | unknown | speB7 | − | I |
| 43 | T8 | 1719 | unknown | unknown | speB7 |  |  |
| 44 | M28 | 587 | scarlet fever | Canada - 1980s | speB18 | − | II |
| 10 | T28 | 289 | SID | USA - 1980s | speB11 |  |  |
| 45 | M24 | 684 | ARF | USA - 1964 | speB12 | − | I |
| 45 | M19 | 1294 | ARF | USA - unknown | speB13 | − | I |
| 46 | M29 | 694 | unknown | Egypt - 1971 | speB16 | − | I |
| 46 | M44 | 1226 | ARF | USA - 1950s | speB22 | + | II |
| 46 | M31 | 427 | unknown | unknown | speB16 | − | I |
| 47 | M30 | 366 | unknown | USA - 1940s | speB13 | − | I |
| 26 | NT | 262 | invasive | USA - 1980s | speB6 |  |  |
| 16 | M66 | 168 | invasive | USA - 1980s | speB25 | + | II |
| 15 | M73 | 302 | invasive | USA - 1950s | speB17 |  |  |
| 14 | M4 | 321 | TSLS | USA - 1980s | speB5 | − | II |
| 48 | M59 | 1882 | unknown | unknown | speB37 | + | I |
| 49 | M5 | 1289 | ARF | USA - 1953 | speB14 | − | I |
| 20 | M18 | 156 | TSLS | USA - 1980s | speB1 | − | I |
|  | M18 | 300 | invasive | USA - 1980s | speB1 |  |  |
| 27 | M6 | 303 | invasive | USA - 1980s | speB6 | − | I |
| 50 | M43 | 1842 | unknown | unknown | speB36 | − | I |
| 51 | M17 | 1233 | ARF | USA - 1944 | speB21 | − | I |
| 52 | M23 | 1901 | unknown | unknown | speB35 | − | I |
| 53 | M49 | 719 | impetigo | Trinidad - 1976 | speB10 | + | II |
| 54 | M15 | 1898 | unknown | unknown | speB32 | + | II |
| 55 | M25 | 686 | wound | USA-1969 | speB9 | + | II |
| 24 | M12 | 590 | SID | Canada - 1980s | speB3 | − | I |
| 24 | M22 | 162 | SID | USA - 1980s | speB28 | + | II |
| 56 | M9 | 800 | impetigo | USA - 1964 | speB20 | + | II |
| 57 | M56 | 1864 | unknown | unknown | speB3 | − | I |
| 58 | M10 | 1896 | unknown | unknown | speB39 |  |  |
| 59 | NT | 1991 | blood | USA - 1993 | speB26 |  |  |
|  | M75 | 758 | ARF | USA - 1986 | speB26 |  |  |
|  | M75 | 1911 | unknown | unknown | speB26 |  |  |
| 5 | NT | 165 | TSLS | USA - 1980s | speB4 |  |  |
| 4 | M2 | 327 | TSLS | USA - 1980s | speB3 | + | II |
| 60 | M9 | 796 | unknown | USA - 1970 | speB19 | + | II |
| 61 | M11 | 650 | NP | Trinidad - 1972 | speB23 | + | II |
|  | M11 | 2075 | invasive | Canada - 1980s | speB null | + | II |
| 62 | M62 | 1883 | unknown | unknown | speB17 | + | II |
| 63 | M13 | 659 | unknown | Egypt - 1971 | speB24 | + | II |
| 64 | PT4931 | 1870 | unknown | unknown | speB31 |  |  |
| 65 | TR2612 | 1872 | unknown | unknown | speB38 |  |  |
| 66 | M27 | 1838 | unknown | unknown | speB30 | − | I |
| 67 | NT | 2017 | pharyngitis | USA - 1991 | speB24 |  |  |
| 67 | NT | 2018 | pharyngitis | USA - 1992 | speB24 |  |  |
| 68 | NT | 1990 | pharyngitis | USA - 1993 | speB27 |  |  |
| 69 | TR2233 | 1914A | unknown | unknown | speB26 |  |  |
| 32 | NT | 317 | invasive | USA - 1980s | speB3 |  |  |

[a]ET, electrophoretic type.
[b]NT; nontypeable for M protein serotype.
[c]MGAS, Musser group A Streptococcus reference number. Strain sources and original designations are as follows: J. C. Huang, Laboratory Centre for Disease Control, Ottawa, Canada, MGAS 579 (11111), 587 (9378), 590 (11078), 2075 (DC 11435); J. E. Peters, Wilford Hall Medical Center, San Antonio, Texas, MGAS 1991 (BB6672-3), 1990 (BA9812-4), P. M. Schlievert, University of Minnnesota, Minneapolis, Minn., MGAS 1253 (119/6. also known as SF130/13), MGAS 1251 (C203S), 166 (Reineke), 285 (195), 325 (89.5.5612), 157 (Zinke), 315 (Soldier 1), 282 (192), 289 (199), 262 (Cal 17), 168 (Reinary), 302 (Lambert), 321 (Weckmuller), 156 (Wilson), 300 (Kluss), 303 (Lundeen), 162 (Cygan), 165 (Wicks), 317 (Timmers);

E. L. Kaplan, University of Minnesota, MGAS 480 (90-441); M. A. Kehoe, University of Newcastle upon Tyne, Newcastle upon Tyne, England, MGAS 1841 (M41), 1871 (PT5757), 1893 (PT4854), 1882 (M59), 1842 (M43), 1901 (M23), 1898 (M15), 1864 (M56), 1896 (M10), 1911 (M75), 1881 (M62), 1870 (PT4931), 1872 (TR2612), 1838 (M27), 1914A (TR2233); D. LeBlanc, University of Texas Health Science Center at San Antonio, Tex., MGAS 1222 (Cole 36XA87), 1226 (Cole 4OXF1), 1233 (Cole 45XA9), K. H. Johnston, Louisiana State University Medical Center, New Orleans, La., MGAS 1719 (B220); D. E. Bessen, Yale University, New Haven, Conn., MGAS 1832 (CS110), 1294 (1RP232), 1289 (1RP144); S. K. Hollingshead, Department of Microbiology, University of Alabama School of Medicine, Birmingham, Ala., MGAS 660 (D469), 789 (1GL100), 807 (D323), 429 (C256/86/3), 684 (1RP284), 694 (D470), 427 (J137/69/1), 366 (AGL130), 719 (D938), 686 (D316), 800 (A724), 758 (86-809), 796 (D339), 650 (D691), 659 (D474). All other strains are from the collection of J.M.M.

$A^d$ TSLS, toxic-shock-like syndrome; SID, severe invasive disease; ARF, acute rheumatic fever; NP, nasopharynx.

EXAMPLE 2

Purification of the Cysteine Protease

Bacteria were grown overnight at 37° C. in 5% $CO_2$ on brain-heart infusion (BHI) agar. The overnight culture was used to inoculate 200 ml of BHI liquid medium, and the culture was incubated for 12–14 hours at 37° C. in 5% $CO_2$. A 50 ml aliquot of the overnight growth was added to 2 liters of chemically defined medium (JRH Bioscience, Lenexa, Kans.), pH 6.0, and the culture was incubated at 37° C. in 5% $CO_2$. The broth was maintained at pH 5.5–6.0 by the addition of sterile sodium bicarbonate (10% w/v). After 8–9 hours, the cells were removed by centrifugation and the supernatant was concentrated to 250 ml by passage through a 10 kDa cutoff spiral ultrafiltration cartridge (Amicon). Buffer exchange (>99%) by diafiltration was conducted with 1.5 liters of 20% ethanol–20 mM Tris-HCl, pH 7.0 (buffer A) at 4° C., and the material was stored overnight at 4° C. The diafiltered solution was passed through a matrix gel red A (Amicon) column (1.5 cm×15 cm) equilibrated with buffer A. The column was washed with buffer A until the adsorption (280 nm) returned to baseline, and the protein was eluted with buffer A containing 2M NaCl. The eluted material was collected as one fraction, and concentrated to 3 ml by ultrafiltration (Centriprep 10, Amicon), and the buffer was exchanged with PBS, pH 7.2, by gel-filtration chromatography (BioRad).

Aminoterminal sequencing of the purified protein derived from dye-ligand affinity chromatography (FIG. 1) reveals a sequence of -QPVVKSLLDSK-, corresponding to amino acids 146–156, thereby confirming the identity of the purified material as the truncated mature active form of streptococcal cysteine proteinase. The enzyme is stable for at least several months at −20° C. Three distinctive speB allelic variants (identified by sequencing studies) have been purified. The zymogen form can be purified with a closely similar protocol, except cysteine is omitted from the medium and the culture is incubated in the absence of supplemental $CO_2$.

The published amino acid sequence for cysteine proteinase, including the configuration of the presumed active site, is incorrect. The predicted amino acid sequence encoded by this sequence is not cognate with the published cysteine protease sequence. Instead, the nucleotide sequence resembles, but is distinct from, the allele described by Hauser and Schlievert. However, the configuration of amino acids around the active cysteine residue is identical in strain B220 and all strains characterized thus far. Therefore, the proposition of Hauser and Schlievert (1990) that the lack of protease activity associated with SPEB purified from their M12 strain 86-858 is a consequence of the difference in amino acid sequence around the Cys residue is incorrect.

EXAMPLE 3

Cleavage of npIL-1β by Streptococcal Cysteine Protease

Figure 2A:
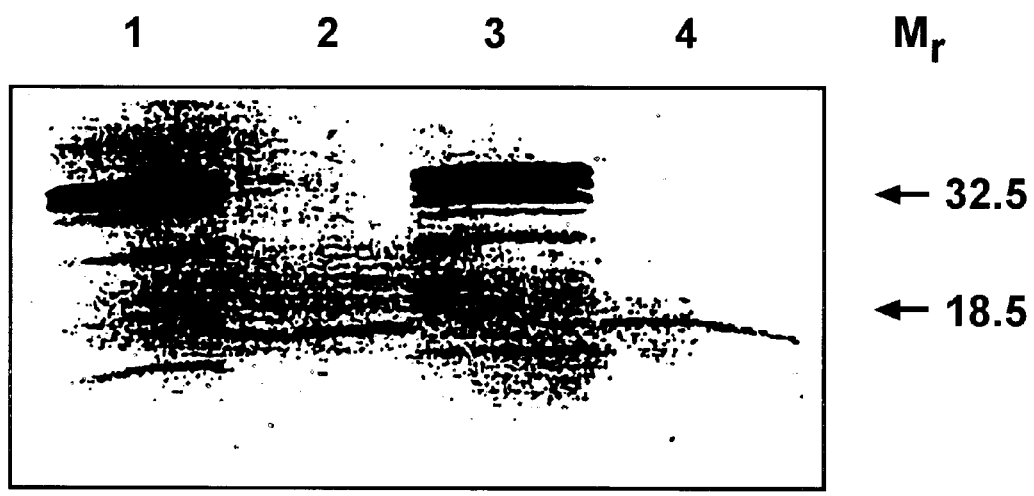
FIG. 2A shows the [$^{35}$S]methionine labeled pIL-1β (lane 1) synthesized in a rabbit reticulocyte lysate system and incubated with 250 ng of purified cysteine protease (lane 2) or boiled cysteine protease (lane 3) for 1 hour. A human pIL-1β Asp 116→Ala 116 mutant was also cleaved by the cysteine protease (lane 4).
Figure 2B:
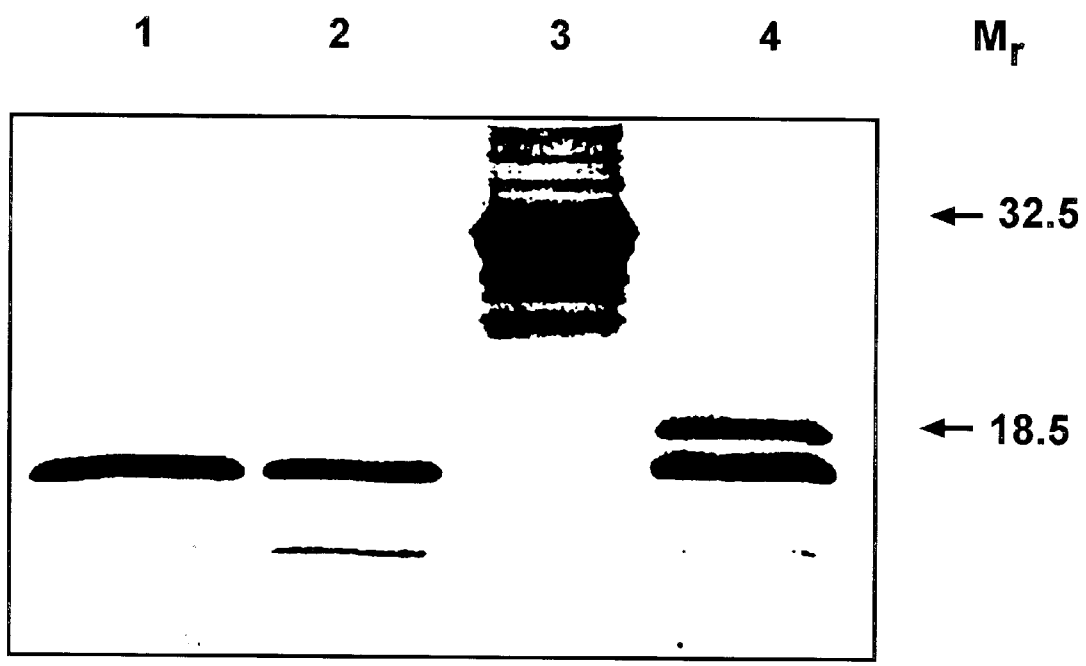
FIG. 2B shows the western immunoblot analysis of mature and recombinant pIL-1β cleavage products. Lane 1:mIL-1β alone; lane 2: mIL-1β plus the cysteine protease; lane 3: pIL-1β alone; lane 4: pIL-1β plus the cysteine protease. Incubations were conducted for 30 minutes at 37° C. The cleavage products were resolved by SDS-PAGE, transferred to nitrocellulose and probed with carboxy-terminal-cysteine protease; lane 3: pIL-1β alone; lane 4: pIL-1β plus the specific monoclonal antibody (specific for IL-1β). The ~18.5 kDa product was converted to the lower molecular weight form upon further incubation. The immunoreactive proteins of greater and less than ~33 kDa in lane 3 are produced in the fermentation process used to make pIL-1β.

An assay employing radiolabeled pIL-1β made in a rabbit reticulocyte transcription-translation system was used. The cysteine protease produced a cleavage product of approximately 18 kDa, a size very similar to the apparent molecular weight of mIL-1β (FIG. 2A). Western blot analysis of the cleavage products generated from recombinant pIL-1β made in E. coli confirmed this result (FIG. 2B).

The cysteine protease cleaved a human pIL-1β mutant (Asp 116→Ala 116, creating an Ala 116 - Ala 117 linkage) that is not degraded by ICE. As observed with wild type pIL-1β, cysteine protease cleaved the mutant substrate to form a product with an apparent molecular weight of ~18 kDa (FIG. 2A). Thus, the primary cleavage site for the cysteine protease was not the ICE proteolytic site.

To determine exactly where the cysteine protease cleaved pIL-1, the aminoterminal 10 amino acid residues of the ~18 kDa product made by degradation of recombinant pIL-1β was sequenced. The cysteine protease cleaved pIL-1β between His 115 - Asp 116 to create a molecule one amino acid residue longer than mIL-1β.

EXAMPLE 4

Normal Biological Activity of the Mature IL-1β Cleavage Product

Figure 3:
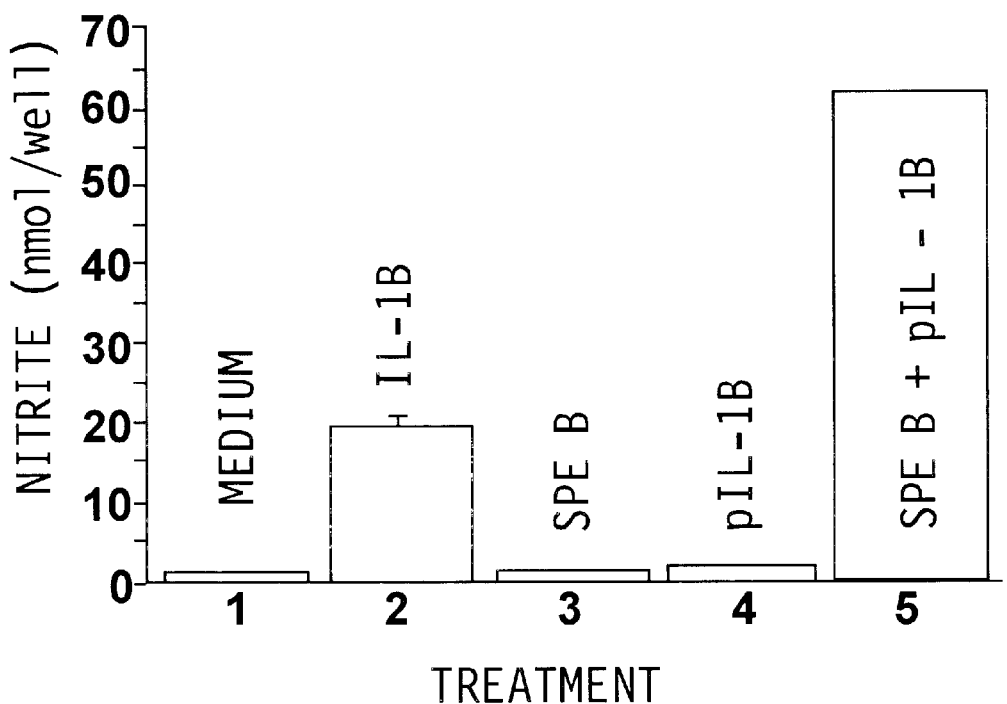
FIG. 3 shows the results of stimulation of nitric oxide (NO) synthase activity by the cysteine protease and pIL-1β in rat aortic smooth muscle cells. Cells were treated for 24 hours with either serum free medium (SFM )(1), mature pIL-1β (3 ng/ml) (2), cysteine protease (4 mg/ml) (3), pIL-1β (~200 ng/ml) (4), or cysteine protease plus pIL-1β (5). The nitrite concentration in conditioned media samples from treated cells was determined by comparison with a sodium nitrite standard curve.

Because a highly active form of mIL-1β with Asp-116 at the aminoterminus was described in the course of characterization of a metalloprotease found in human peripheral blood mononuclear cells, cysteine protease was processing inactive pIL-1β to biologically active IL-1β. Mature IL-1β is a potent inducer of nitric oxide synthase (NOS) activity in vascular smooth muscle cells (SMC). Cysteine protease was added in the presence or absence of pIL-1β to confluent cultures of SMC and NOS activity was assayed by measuring nitrite anion levels in the medium after 24 hours. Neither cysteine protease nor pIL-1β alone produced a significant increase in nitrite levels. In contrast, addition of cysteine protease and pIL-1β together caused approximately a 60-fold increase in nitrite accumulation (FIG. 3).

IL-1β generated by cysteine protease cleavage of pIL-1β was also found to be active in the A375 cell line assay. In an assay in which approximately 500 ng/ml of intact pIL-1β was inactive, a cysteine protease digest of this material yielded $6.1 \times 10^4$ units/ml of activity; 500 ng/ml of authentic IL-1β corresponded to $1.1 \times 10^5$ units in this assay.

EXAMPLE 5
Cleavage Activity of Variant Cysteine Protease Enzymes

Figure 4:
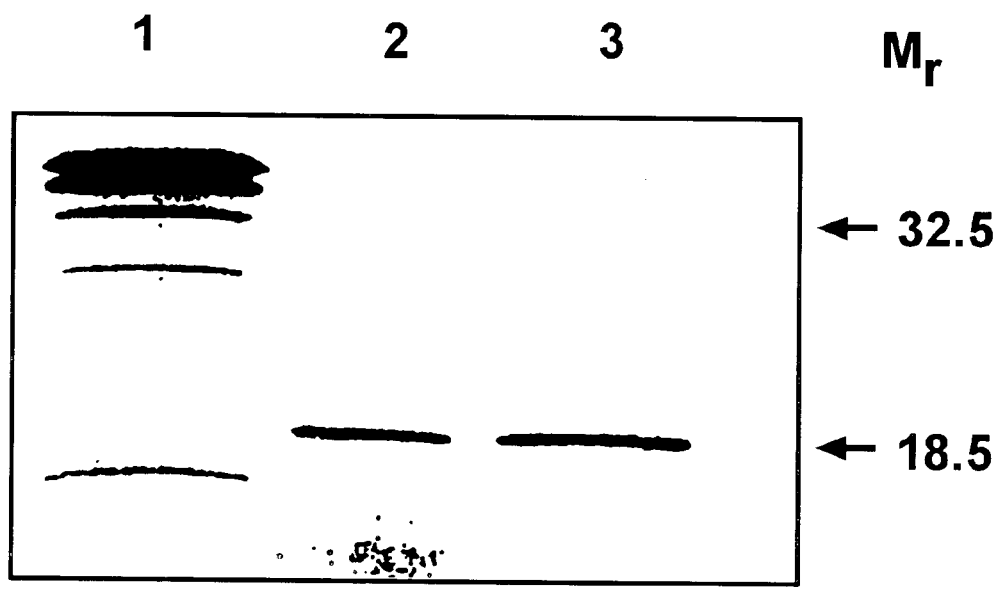
FIG. 4 shows the results of cleavage of pIL-1β by allelic variants of Streptococcal cysteine protease. Rabbit reticulocyte lysate containing [$^{35}$S]methionine-labeled pIL-1β (lane 1) was incubated with cysteine protease purified from strain MGAS 279 (lane 2) or MGAS 289 (lane 3) as described for FIG. 2A.

Two additional naturally occurring cysteine protease allelic variants (SPE B2 and SPE B11) also produced an IL-1β fragment with an apparent molecular weight identical to that made by SPE B7 purified from MGAS 1719 (FIG. 4).

EXAMPLE 6
Sequencing of speB

The speB gene was amplified by the polymerase chain reaction (PCR), with synthetic oligonucleotide. The DNA fragment studied (1.437 bp) represents the entire coding region (1,197 bp) and 160 bp of upstream and 80 bp of downstream sequence. For about one-third of the strains, single-stranded DNA was prepared by the lambda exonuclease method and sequenced in both orientations with Sequenase version 2.0. Variant alleles were sequenced again to confirm the nucleotide changes.

Basically, the sequencing of the cysteine protease structural gene was as follows. The cysteine protease structural gene was amplified by the polymerase chain reaction (PCR), with synthetic oligonucleotides. The oligonucleotide primers used to amplify speB and flanking regions were as follows:

SPEB-X (SEQ ID NO:9), 5'-GTTGTCAGTGTCAACTAACCGT 3'; and

SPEB-2 (SEQ ID NO:10), 5'=ATCTGTGTCTGATGGATAGCTT-3'.

The following four oligonucleotides were used as internal sequencing primers:

SPEB-1 (SEQ ID NO:11), 5'-CTTTCTGGCTCTAATATGTATGT-3';

SPEB-3 (SEQ ID NO:12), 5'-GTTATTGAAAAAGTAAAACC-3';

SPEB-4 (SEQ ID NO:13), 5'-TTTTCAATAACAGGTGTCAA-3'; and

SPEB-Y (SEQ ID NO:14), 5'-TCTCCTGAAACGATAACAAA-3'.

PCR amplification of 1 μl of chromosomal DNA was performed in 100 μl of a mixture containing 50 mM KCl, 10 mM Tris-HCl, pH 8.3, 1.5 mM MgCl$_2$, 0.001% gelatin, 200 μM each of DATP, dCTP, dGTP, and dTTP, 200 nM each of SPEB-X and SPEB-2, and 2.5 units of AmpliTaq DNA polymerase. The thermocycling parameters were denaturation at 94° C. for 1 minute, annealing at 55° C. for 2 minutes, and extension at 72° C. for 2.5 minutes for a total of 30 cycles. A final extension at 72° C. for 15 minutes was used.

The DNA fragment (1,437 bp) represents the entire coding region (1,197 bp) and 160 bp of upstream and 80 bp of downstream sequence. For about one-third of the strains, single-stranded DNA was prepared by the lambda exonuclease method and sequenced in both orientations with Sequencase version 2.0. Variant alleles were sequenced again to confirm the nucleotide changes.

The protease gene in approximately two-thirds of the strains was characterized by automated DNA sequencing with an Applied Biosystems, Inc., Model 373A instrument. For the automated approach, the gene was amplified with PCR (10 mM Tris-HCl, pH 8.3; 50 mM KCl; 1.5 mM MgCl$_2$; 2.5 units of Taq polymerase; 20 picomoles of each primer; 1 μL of chromosomal DNA template), with the following thermocycler parameters: denaturation at 94° C. for 4 minutes, 30 cycles of denaturation at 94° C. for 1 minute, primer annealing at 55° C. for 2 minutes, extension at 72° C. for 2 minutes, and a final extension at 72° C. for 5 minutes. The unincorporated nucleotides and primers were removed by filtration through Microcon 100 microconcentrators (Amicon Inc., MA). Sequencing reactions with the Taq DyeDeoxy terminator cycle sequencing kit (Applied Biosystems, Inc., CA) were performed with 7 μL of PCR amplified DNA as template and 3.2 picomoles of primer. The unincorporated dye terminators and primers were separated from the extension products by spin column purification (Centri-Sep, Princeton Separations, Inc., NJ). The sample was dried in a vacuum centrifuge. Prior to gel loading, the sample was resuspended in 4 μL of sample loading buffer (5:1 deionized formamide; 50 mM EDTA, pH 8.0) and heat denatured for 2 minutes at 90° C. The data were assembled and edited with EDITSEQ, ALIGN, and SEQMAN programs (DNASTAR, WI).

EXAMPLE 7
Estimates of Genetic Relationships Among Clones

Methods of estimating genetic relationships among *S. pyogenes* clones by multilocus enzyme electrophoresis were as described by Musser et al., *Proc. Natl. Acad. Sci. U.S.A.* 88:2668–72 (1991). Thirty-six ETs not identified previously were arbitrarily numbered ET 34 - ET 53.

EXAMPLE 8
speB Allele in Strain B220 (Elliott 5797)

The speB gene (speB7) in strain MGAs 1719 does not encode a protein with the amino acid sequence presented previously. There are discrepancies between the protein sequence from strain B220 and a speB allele (herein designated speB1) in a serotype M12 strain (86-858).

EXAMPLE 9
speB Alleles and Disease Type

The present invention demonstrates that streptococcal clones with the same speB allele, and speB allele - M protein combination are associated with several different diseases. For example, strains of ET 1 - Ml - speB2 were cultured from patients with pharyngitis, scarlet fever, cellulitis, and TSLS; and ET 2 -M3 - speB3 organisms were recovered from cases of pharyngitis, scarlet fever, and TSLS. Similarly, strains cultured from individuals with acute rheumatic fever had six distinct speB alleles. Hence, there was no apparent preferential association of speB allele and disease type.

The identification of the speB allele in a strain (MGAS 789) recovered in the 1940s expressing M1 protein, but assigned to ET 36 rather than ET 1 like contemporary M1 strains suggests that variation in speB allele—multilocus enzyme genotype—M protein associations made by a contributing factor in temporal changes in streptococcal disease frequency and severity.

EXAMPLE 10
speB Variation, M Protein Class, Opacity Factor Phenotype, and vir Regulon Architecture The present invention found no compelling evidence for an analogous differentiation of speB allelic variants. Strains assigned to either of two distinct classes based on reactivity with a panel of monoclonal antibodies to M protein did not have consistent sequence differences, and in several instances the identical speB allele was found in strains of two M protein classes. For example, the speB3 allele occurred in strains of both class I (M3 and M12) and class II (M2), and similarly, the speB5 allele was identified in strains expressing M1 and M4 assigned to class I and class II, respectively (Table I). Similarly, there was no simple congruent relationship between speB allele and vir regulon architecture or opacity factor phenotype. M2, M3, and M12 strains all had the speB3 allele, but, M3 and M123 are opacity factor-negative and M2 is opacity factor-positive. The lack of a significant correlation between M serotype class and speB phylogeny could also be caused by relatively frequent lateral transfer events involving part or all of the emm and speB genes.

EXAMPLE 11
Cleavage of purified extracellular matrix (ECM) proteins

Figure 5A:
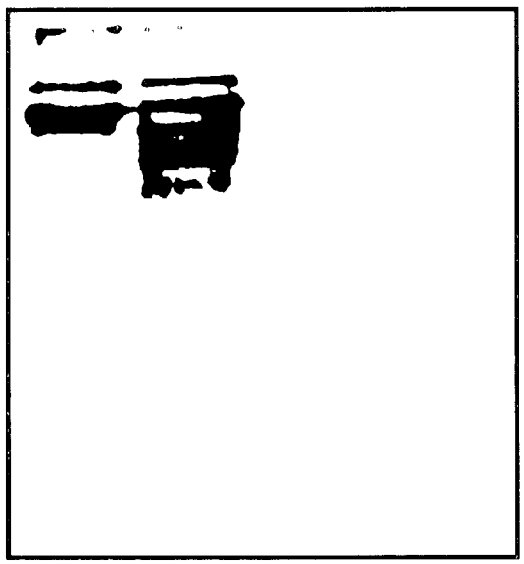
FIG. 5 shows the results of cleavage of purified extracellular matrix (ECM) proteins.
Figure 5B:
Figure 5C:
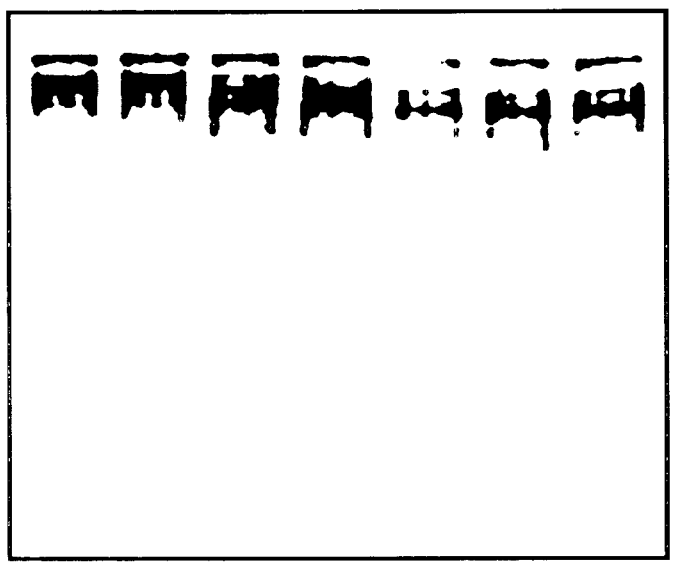

Streptococcal cysteine protease rapidly degrades purified vitronectin (VN) (FIG. 5). After five minutes of protease incubation with VN, degradation products could not be identified by either Coomassie blue staining or immunoblotting with polyclonal anti-VN antibodies. Similarly, the streptococcal protease cleaved fibronectin (FN) immediately, as shown by the rapid appearance of lower molecular weight products (FIG. 5). However, in contrast to VN degradation, FN cleavage apparently occurred at a limited number of specific sites (FIG. 5) of manuscript). Incubation of FN with the protease for up to 12 hours did not result in formation of additional degradation products.

No significant cleavage of human laminin (LN) was observed under the experimental conditions assayed (FIG. 5), or when 10 μg of protease and 2 μg of LN substrate were used.

Figure 6A:
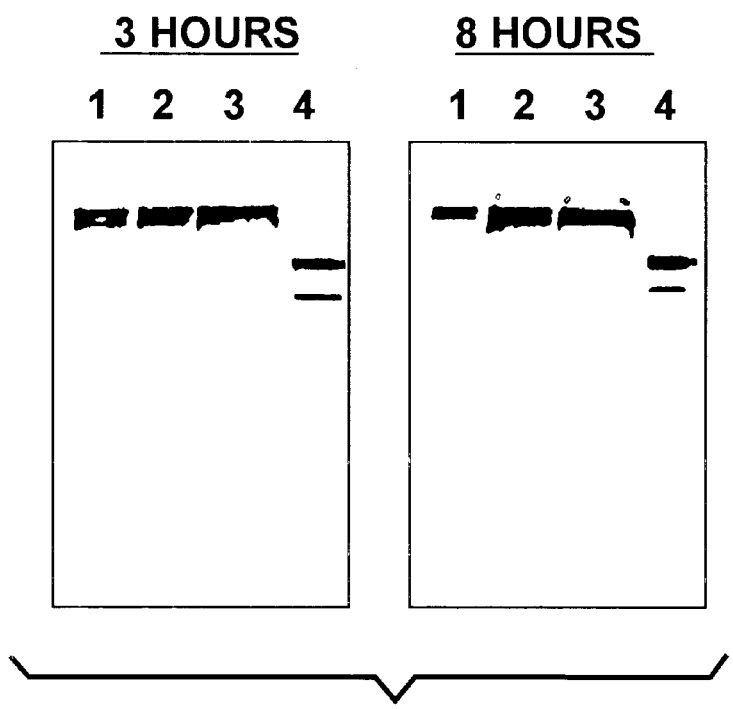
FIG. 6 shows the induction of cytopathic effect and fibronectin cleavage in human umbilical vein endothelial cell (HUVEC) cultures.

EXAMPLE 12
Induction of cytopathic effect and fibronectin cleavage in human umbilical vein endothelial cell (HUVEC) cultures Because patients with invasive *S. pyogenes* episodes frequently have bacterial sepsis with endothelial cell damage, the ability of the streptococcal cysteine protease to cleave FN directly from HUVECs grown in culture was examined. Western immunoblot analysis of cells in the absence of protease, or treated with boiled protease for up to 8 hours, showed no detectable FN degradation of (FIG. 6). In contrast, cells incubated with as little as 6 μg/ml of streptococcal protease per well for 2 hours retained only a small fraction of intact native FN. Thus, the streptococcal protease cleaves FN in a dose and time dependent manner in the complex environment of cells growing in tissue culture.

Interestingly, treatment of HUVECs with the streptococcal protease rapidly induced striking cytopathic effects (FIG. 6). By 3 hours after protease addition, zones of clearing occurred in the cell monolayer. This effect was followed by loss of cell adherence to the matrix and ablation of the characteristic cobblestone morphology. FN cleavage was detectable by immunoblot analysis prior to the onset of cytopathic effect. Bands that correspond to native human VN in either the solubilized control or treated HUVECs by western immunoblot analysis were not seen, presumably due to low level or lack of VN expression by these cells.

EXAMPLE 13
Cysteine protease production by *S. pyogenes* strains

Figure 7:
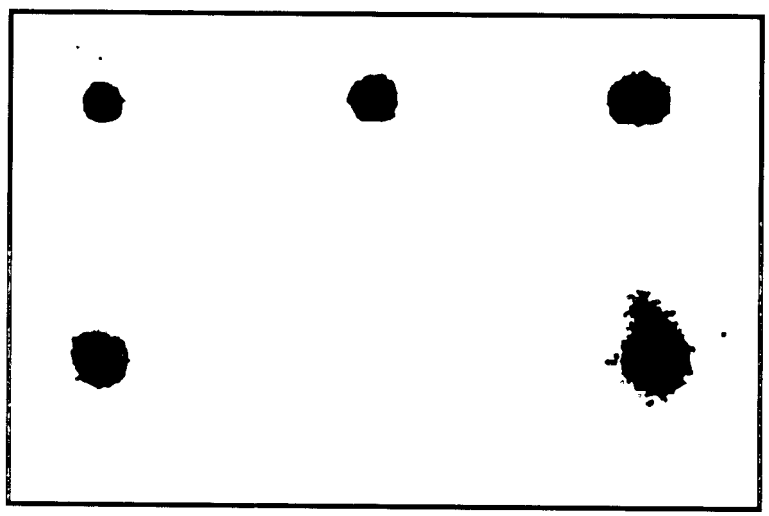
FIG. 7 shows SPE B production by *S. pyogenes* strains.
Figure 8:
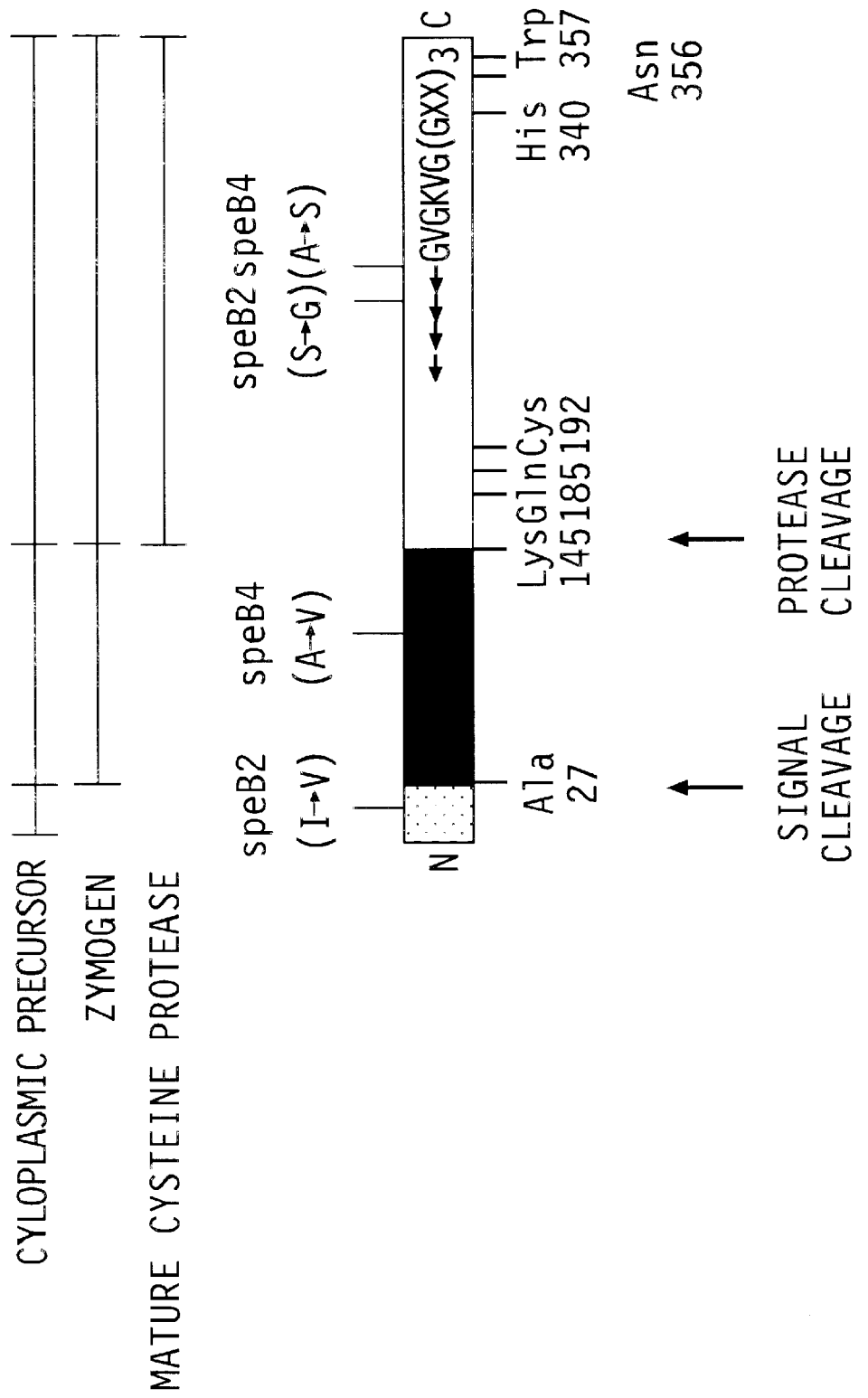
FIG. 8 shows the processing sites, locations of amino acid variations found in the proteins made by the speB2 and speB4 alleles, and amino acids that are targets for mutation.
Figure 9:
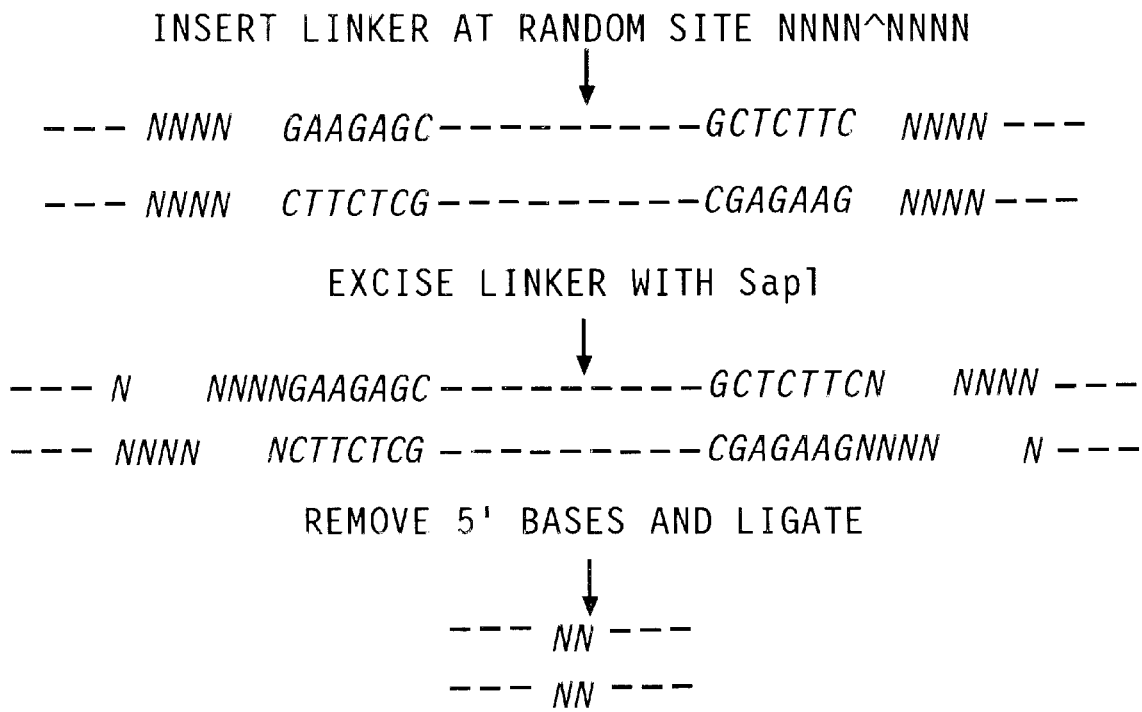
FIG. 9 shows the generation of random mutations in speB.
Figure 10:
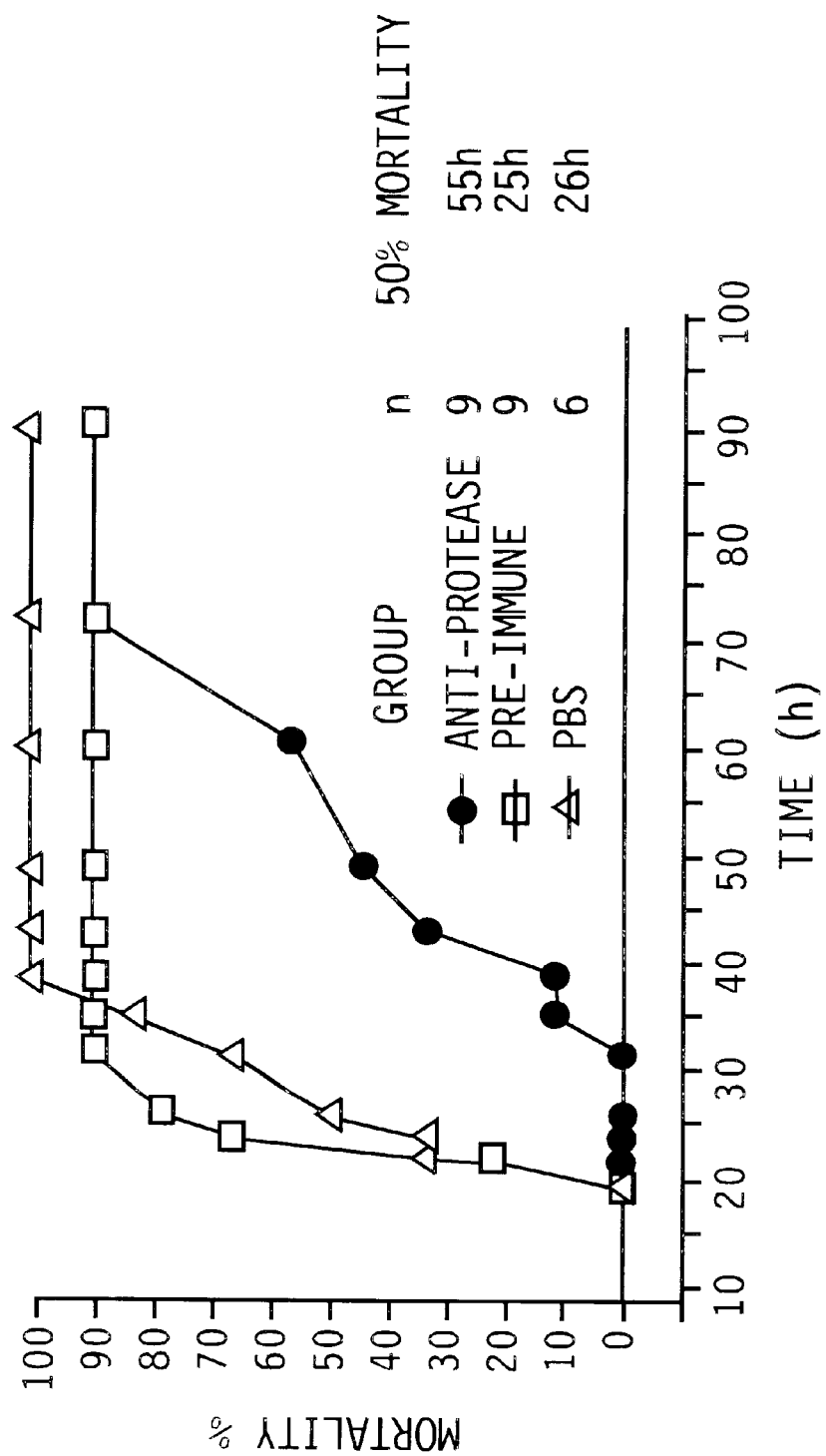
FIG. 10 shows protection with rabbit anti-cysteine protease IgG in mice. Mice were injected i.p. with 0.1 ml of 1 mg rabbit antibody (IgG) in PBS (pH 7.4) raised against cysteine pretease purified from strain MGAS 1719, which has speB7 allele and procudes the SPE B 4 mature SPE B variant. The antibody was raised in rabbits against purified protease excised from SDS polyacrylamide gel. Control animals received either an equal amount of pre-immune antibody (0.1 ml containing 1 mg of IgG in PBS, pH 7.4) from the same rabbit used as the source for the anticysteine protease antibody, or 0.1 ml of PBS. After 30 minutes, mice were injected i.p. with approximately 100 cfu of strain MGS 315, which has the speB3 allele and produces the SPE BI mature SPEB variant and is an ET2/m3 organism from a case of TSLS in (Musser et al. 1993). The times required for 50% mortality for the mice groups are as follows: PBS, 26 hours; pre-immune, 25 hours, anti-cysteine protease, 55 hours.

Virtually all clinical isolates of Group A streptococci produce SPE B/cysteine protease and patients infected with Group A streptococci develop antiproteinase antibodies. Immunoblot analysis of culture supernatants was used to assess production of SPE B/streptococcal protease by strains of *S. pyogenes,* and one naturally occurring serotype M11 isolate (MGAS 2075) reported to lack speB. With the exception of the three strains, all 64 other isolates examined produced cysteine protease, a result consistent with the notion that virtually all *S. pyogenes* strains express the molecule extracellularly (FIG. 7 and Table I). The three strains had alleles speB3, speB13, and speB16, but other isolates with these same alleles produced the protease. Therefore, all 39 speB alleles can be expressed by Group A streptococcal strains under appropriate conditions. The polymorphic site of the 39 alleles within the 160 bp upstream noncoding region and 1197 bp coding region fo the speB gene are shown in FIG. 11.

EXAMPLE 14
Specific antisera raised against the active cysteine protease

Purified protease (100 μg) mixed with Freund's complete adjuvant was injected subcutaneously at multiple sites into two rabbits. Subsequent immunizations with the purified protease mixed with Freund's incomplete adjuvant were conducted at bi-weekly intervals for a total of five injections. Serum was collected and immunoglobulin purified by FPLC with a protein G-Sepharose column (Pharmacia). Western immunoblot analysis revealed the presence of specific antiprotease reactivity in the post-immunization samples but not in the pre-immunization sera. These rabbits are being maintained and bled at regular intervals to collect large quantities of specific antiserum. This procedure has been described in Kapur. et al. *Microb. Pathog.* (1993), 15:327–46.

EXAMPLE 15
Mouse monoclonal antibodies against the purified mature cysteine protease Monoclonal antibodies against the purified mature cysteine protease were prepared. A dose of 10 μg of SDS-PAGE purified mature protease has been injected a total of five times intraperitoneally into five mice (Balb/c background). Western immunoblot analysis has demonstrated that all mice have serocoverted. The spleens were harvested and fusions performed by standard protocols. Characterization of protease-specific monoclonal antibodies is by standard procedures.

EXAMPLE 16
Measurement of antibody levels

An ELISA has been developed to measure antibody levels against the cysteine protease. Briefly, 10 μg of protease in carbonate-bicarbonate buffer (pH 9.6) was added to each well of a 96-well microtiter plate and incubated overnight at 4° C. The wells were rinsed three times with washing buffer (PBS (pH 7.4) - Tween 20 (0.05%)) and blocked with 200 μL of 0.5% BSA in PBS, pH 7.4, for 2 hours at 37° C. After washing, the wells were charged with 100 μL of a serial dilution of test antisera (1:100 through 1:1600 of rabbit serum). The plate was incubated for 1 hour at 37° C., washed again, and 100 μL of a 1:5000 dilution of extravidin-alkaline phosphatase was added to each of the test wells and incubated at 37° C. for 30 minutes. After washing, 100 μL of alkaline phosphatase substrate (pNPP) was added to each well and reacted for 1 hour at room temperature. The O.D. (405 nm) was read with a microtiter plate reader.

EXAMPLE 17
Immunodot-blot assay for cysteine protease expression

A dot-blot assay was developed that detects as little as 1 nanogram of cysteine protease. Briefly, test material (usually protein precipitates of culture supernatants from bacteria grown in chemically defined medium) was spotted onto a nylon membrane, and unabsorbed sites were blocked by incubation with 0.5% blocking agent (Amersham) for 1 hour at room temperature. The membrane was rinsed with PBS (pH 7.4) - Tween 20 (0.05%) and incubated for 30 minutes with purified polyclonal rabbit antiserum (1:500 dilution) directed against the cysteine protease. The membrane was rinsed with PBS, a secondary antibody (goat anti-rabbit- HRP conjugate, 1:2000 dilution) was added and incubated for 30 minutes at room temperature. The blot was visualized with chemiluminescence (ECL developing reagents, Amersham). With this technique, many isolates previously reported to lack SPEB production based on less sensitive conventional immunologic assays express the cysteine protease.

EXAMPLE 18

Antibody directed against cysteine protease

The immunoprophylactic protection of cysteine protease is seen by the use of two models. First, the intranasal immunization model is used as developed by Bessen and Fischetti (1988) to evaluate the effect of cysteine protease immunization on mucosal colonization by S. pyogenes. Second, a mouse cutaneous infection model (Bunce et al., 1992) is used against a subcutaneous bacterial challenge. Briefly, the animals are injected with protease s.c. on the flank and observed daily, including weight measurements. Abscess volumes and area of dermonecrosis is calculated and lesion size curves are determined.

EXAMPLE 19

Preparation of Synthetic Peptides of Cysteine Protease

Synthetic peptides based on cysteine protease may also be used as immunogens in the preparation of a vaccine against Group A streptococcal infections. Several synthetic peptides are selected based on the location of allelic variation and conservation and the cysteine protease antigenic index generated with a Jameson-Wolf plot. First, each of the following three peptides are used. These peptides correspond to the variable region (amino acids 308 to 317) in mature streptococcal cysteine protease containing two of the six major calculated antigenic peaks.

Peptide 1 (SEQ ID NO:15): H-Q-I-N-R-S(308)-D-F-S-K-Q-D-W-E-A(317)-Q-I-D-K-E

Peptide 2 (SEQ ID NO:16): H-Q-I-N-G(308)-D-F-S-K-Q-D-W-E-A(317)-Q-I-D-K-E

Peptide 3 (SEQ ID NO:17): H-Q-I-N-S(308)-D-F-S-K-Q-D-W-E-A(317)-Q-I-D-K-E

Subsequently, each of the following four peptides, which correspond to four invariant calculated antigenic peaks are used for immunization.

Peptide 4 (SEQ ID NO:1): P(171)-V-I-E-K-V-K-P-G-E-Q-S-F-V-G-Q

Peptide 5 (SEQ ID NO:2): Y(203)-H-N-Y-P-N-K-G-L-K-D-Y-T-Y-T-L

Peptide 6 (SEQ ID NO:3): P(247)-T-Y-S-G-R-E-S-N-V-Q-K-M-A-I

Peptide 7 (SEQ ID NO:4): I(344)-D-G-A-D-G-R-N-F-Y-H

Naturally occurring variant zymogens and cysteine protease display unique linear B-cell epitopes.

Overlapping 10-mer peptides are used which overlap 2 amino acid residues with the previous one in the consecutive primary sequence corresponding to 371 amino acids of the mature cysteine protease zymogen (translated product minus leader sequence). Synthetic 10-mers corresponding to the 10 variant amino acid residues will also be used. The variant amino acids are positioned in the middle of the 10-mer. For example, if the sequence of a 10-mer corresponding to one region of the SPEB1 variant is position 304-QINRSDFSKQ-313 (SEQ ID NO:18), then 304-QINRGDFSKQ-313 (SEQ ID NO:19) is also examined, a 10-mer that incorporates a variant amino acid found in the SPEB2 variant. Once the 10-mer peptides are synthesized, an ELISA is used to examine the reactivity of all peptides with the following materials: (i) rabbit polyclonal hyperimmune antiserum made against purified cysteine protease (positive control), (ii) rabbit pre-immune serum (negative control), (iii) our panel of 28 murine monoclonal antibodies raised against purified cysteine protease, (iv) acute and convalescent sera obtained from 20 patients with necrotizing fasciitis and/or TSLS in Canada (obtained from D. Low, Mount Sinai Hospital, Ontario, Canada), 5 USA patients with TSLS characterized by extensive soft tissue destruction (obtained from D. Stevens, V.A. Hospital, Boise, Id.), and 5 patients with ARF (obtained from A. Bisno, University of Miami Medical School). The great majority of the synthetic peptides usually are not reactive with each sera and there are a large number of internal redundant negative control peptides. Sera dilutions are used in these assays (1:1000 for hyperimmune rabbit antiserum, 1:500 for human serum, and 1:5–1:10 for MAb culture supernatants).

To determine the linear B-cell epitopes, for each sera and MAb tested, $OD_{405}$ is plotted versus 10-mer peptide number. The linear B-cell epitopes are displayed as a peak in the $OD_{405}$ values. In general, a peak is composed of several contiguous overlapping peptides, and the 10-mer peptide with the highest $OD_{405}$ value is defined as the parent peptide.

The pro region contains at least one unique linear B cell epitope. The same linear B cell epitopes will most likely be recognized by all 15 human convalescent sera specimens.

EXAMPLE 20

Creation of mutant speB proteins

FIG. 8 shows the processing sites, locations of amino acid variations found in the proteins made by the speB2 and speB4 alleles, and amino acids that are targets for mutation. Both site-directed and random mutagenesis schemes are employed to identify residues that disrupt cysteine protease function and zymogen processing, and to map regions that constitute antigenic domains of the protein. Targets for functional amino acid replacement are based on biochemical analysis of cysteine protease (Tai, et al., 1976) and by analogy with similar residues in eukaryotic cysteine protease.

To create a stable zymogen to facilitate crystallographic studies and generate enzymatically deficient or inactive protease for structure-function studies, mutant forms of the cysteine protease protein are made and characterized. A target mutagenesis scheme creates changes that: (i) disrupt protease activity; (ii) prevent zymogen processing; (iii) prevent substrate binding; and (iv) alter immunoreactivity. Amino acids are changed to structurally neural alanine. A mutant protein that lacks protease activity, but which retains antigenicity, is generated by mutagenesis of the single cysteine residue (Cys-192→Ala-192) at the catalytic site of the molecule. Also, His-340 and Gin-185 and Asn-356 are mutagenized. These three changes are epistatic to the Cys-192 mutation, but may alone exhibit altered activity. Trp-357, thought to be involved in substrate binding and similarly positions within papain, is also to be targeted. A stable zymogen precursor is also created by mutating residues surrounding the protease cleavage site at Lys-145. In addition, mutagenesis of Cys-192 may prevent autoproteolysis, as occurred for a Cys→Ser mutant of papain, the prototype cysteine protease. Other mutagenesis targets include a putative nucleotide binding domain (GVGKVG) (SEQ ID NO:6) and a potential collagen docking region [$(GXX)_3$] within carboxy terminal portion of the protein. Site-directed mutagenesis is used, by the charged-to-alanine-scanning method, to substitute positively and negatively charged amino acids (often involved in recognition and activity) with alanine. Many of the charged residues (14 lysine, 7 arginine, 12 aspartate, and 76 glutamate residues in the mature peptide) are expected to lie on the surface of the cysteine protease structure, and some are expected to define epitopes on the molecule. In particular, a region of charged amino acids, from 307 to 321 (8/15 charged), is examined; this region includes the site of speB and speB4 amino acid substitutions. Residues in antigenic regions identified in the epitope mapping studies are also mutated.

First, the speB gene is amplified from an ET1/M1 S. pyogenes strain, with PCR, and the product is cloned into a multicopy filamid vector such as pBluescript (Strategene, La Jolla, Calif.). This vector is chosen because it carries the regulated lac promoter and can be replicated as a single-stranded molecule for site-directed mutagenesis. Cloning is designed to place the promoter, ribosome binding site and speB reading frame 3' to the inducible lac promoter on the vector so that the protein can be conditionally over-expressed in *E. coli* when the lac inducer, IPTG, is added. The speB promoter is included requiring expressing in *S. pyogenes.* Whole cell extracts and periplasmic shockates of *E. coli* cells carrying this primary speB clone are examined for the presence of the cysteine protease protein by SDS-PAGE and by Western blotting with anti-cysteine protease antibody. The resulting plasmid is the target for mutagenesis.

Oligonucleotide-directed mutations, such as substitutions, deletions and small insertions, are created on uracil-containing single-stranded templates by the method of Kunkel (Kunkel, 1985). When possible, mutagenic primers are designed to incorporate a unique restriction site into the speB gene for mapping and mutant selection. Both single and multiple alanine substitutions are created at the residues indicated above. Once residues critical to function are identified, small regions surrounding them are deleted or substituted, by using the same methods, to further characterize the region and to preclude reversion. When crystallographic data is available, additional amino acids are mutated.

A random mutagenesis scheme is also employed. Variant proteins created by this method are most useful for epitope screening, although molecules with altered kinetics and substrate recognitions may also be recovered. Regions of the speB sequence are randomized with mixed oligonucleotides in the primed-mutagenesis protocol, or short, in-frame deletions within the gene are created with a modification of the DNAse 1-linker insertion/deletion protocol of Palzkill and Bostein (Palzkill and Bostein, 1991). Here, synthetic "excision linkers" are first ligated to randomly linearized target DNA, then excised with flanking nyucleotides to create small substitutions or deletions. For example, a linker with two copies of the recognition sequence for the enzyme SapI (GCTCTTC) is used to create six base deletions (three bases on each end of the linker), or random two amino acid deletions, across the speB gene, as illustrated in FIG. 9. Flanking bases are also randomized by filling the ends of the target sequence after linker excision, then inserting a second blunt end linker that includes a random sequence in place of the Ns. The second linker is then removed by digestion with SapI and the target sequence is ligated to generate substitutions.

To identify protease minus mutations, *E. coli* cells producing potential mutant proteins are first screened for protease activity on casein agar plates. Since secretion of cysteine protease to the periplasm is expected, it is possible that protease activity can be observed on plates. If this screening strategy is successful, then thousands of colonies are rapidly examined for functional mutations in cysteine protease. If cysteine protease must be completed secreted from *E. coli* to exhibit activity, then osmotic shockates of each presumptive mutant strain is assayed for proteolytic activity.

EXAMPLE 21

Passive immunization of mice

Passive immunization with rabbit antibody directed against purified denatured cysteine protease partially protects mice against challenge with live *S. pyogenes* (FIGS. 10 and 12). The ability of rabbit antibody raised against purified cysteine protease to protect mice challenged intraperitoneally with a lethal dose of live *S. pyogenes* was examined.

The method used is as follows.

*S. pyogenes* isolate MGAS 1719 is identical to strain B220. This isolate expresses T8 serotype, and has the speB7 allele, and was used as the source strain for cysteine protease purification. Isolate MGAS 315 was recovered in the 1980s from a patient with toxic-shock-like syndrome. The organism is electrophoretic type (ET) 2, expresses serotype M3 protein, and was used as the challenge strain. This isolate also synthesizes SPEA and SSA. Streptococcal cysteine protease was purified from strain MGAS 1719 culture supernatants with a combination of ultrafiltration and dye-ligand affinity chromatography, as described in Example 2. SDS-polyacrylamide gel electrophoresis and coomassie blue staining of the resulting proteolytically active material showed a single major band of $M^r$~30 kDa. The purified cysteine protease preparation does not react with rabbit antiserum raised against acid extracts of M serotype 1 or 3, or type T8 *S. pyogenes* isolates by either western immunoblot or ELISA, but reacted strongly with rabbit antibodies raised against the streptococcal cysteine protease. (FIG. 15).

The minimum lethal dose (MLD) of bacteria was calculated for isolate MGAS 315. Bacteria were grown in brain heart infusion broth (Difco, MI) for 12 h at 37 C, the $A_{600}$ was adjusted to 0.7 (representing ~$10^8$ cfu/ml) with sterile BHI broth, and 0.1 ml of $10^0$ through $10^7$ dilutions of bacteria made in sterile broth were injected intraperitoneally to each of five male 22–24 g CD-1 outbred mice (Charles River, Mass.). The bacterial suspensions were tested for purity before and after the inoculations, and the number of cfu injected per mouse was verified by colony counts. The mice were monitored for a period of 5 days post-inoculation and surviving mice were euthanized with methoxyflurane. Heart blood was collected for bacterial isolation from the mice that died or were sacrificed. The MLD was determined to be the highest dilution at or below which none of the mice in the group survived.

Minimum lethal dose

The minimum lethal does (MLD), the highest dilution of *S. pyogenes* strain MGAS 315 at and below which there were no surviving mice, was approximately 10 organisms per inoculum, indicating that the strain MGAS 315 is unusually virulent to mice when administered via the intraperitoneal route. Pure cultures of Group A Streptococci were recovered from the heart blood of all mice that died after bacterial challenge.

The preparation of rabbit antiserum against streptococcal cysteine protease has been described in Kapur. et al.. *Microb. Pathlg.,* (1993) 15:327–46. Male 22–24 g CD-1 outbred mice were intraperitoneally inoculated with 0.1 ml PBS (n=6) 1 mg immune rabbit IgG in PBS (n=9), or 1 mg pre-immune rabbit IgG in PBS (n=9) and challenged with the MLD of strain MGAS 315, 30 min after the administration of the treatment. The mice were monitored at 3 h intervals and mortality was recorded. Heart blood was collected from dead mice and plated onto BHI agar, and incubated for 48 h at 37 C in 5% $CO_2$. Kaplan-Meier survival curves were plotted and the logrank test was employed to test for statistical differences in survival.

Figure 12:
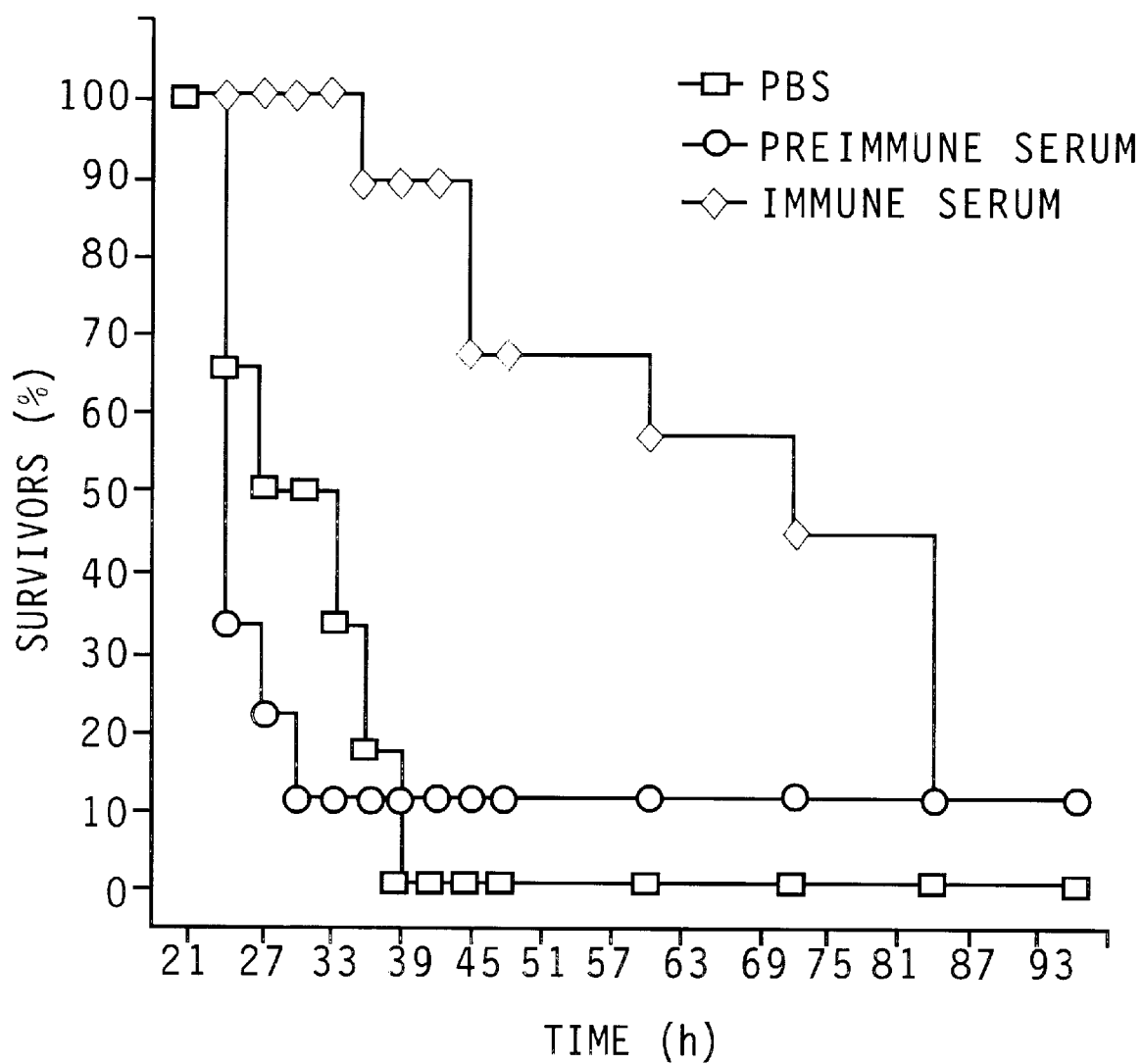
FIG. 12 shows the results of passive administration of anti-protease antibody which protects mice against lethal challenge with heterologous *S. pyogenes*. Intraperitoneal administration of rabbit antibody directed against Streptococcal cysteine protease confers significant protection against lethal challenge with the highly virulent *S. pyogenes* isolate MGAS 315 when compared with control animals that were given PBS or rabbit pre-immune serum.
Figure 13:
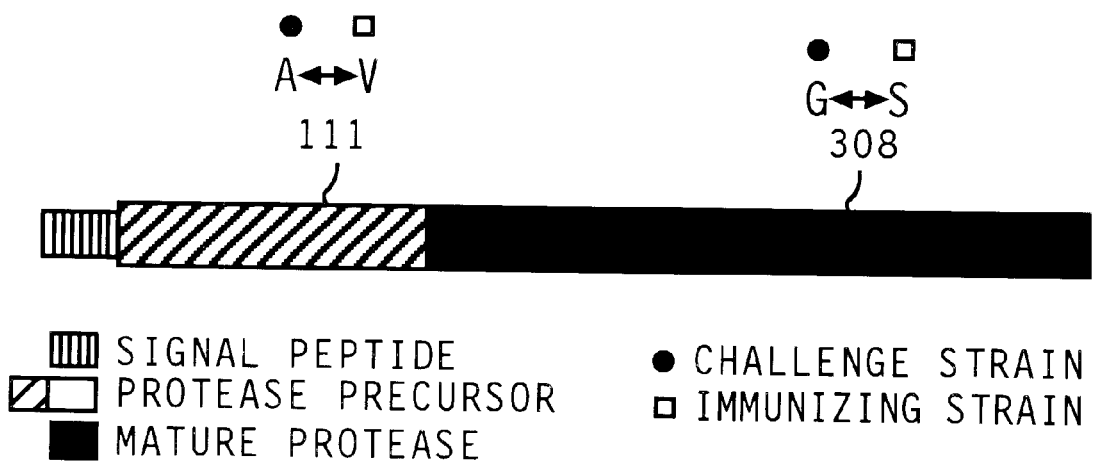
FIG. 13 is a schematic representation of amino acid substitutions in the streptococcal cysteine protease and protease precursor in the challenge strain (●) and the protease to which the antiserum was raised (□). A short peptide fragment of the protease surrounding amino acid 308 contains immunodominant epitopes recognized by mouse polyclonal and monoclonal antibodies (Kapur and Musser, manuscript in preparation). The single letter amino acid abbreviations are A, Ala; V, Val; G, Gly; S, Ser.

The results (FIG. 12) show that passive immunization with rabbit antibody directed against gel-purified denatured cysteine protease confers significant protection against challenge with highly virulent S. pyogenes strain MGAS 315 when compared with control animals given phosphate buffered saline (PBS) or pre-immune serum controls (log rank test; $X^2$; P>00.001). The protection afforded by passively administered antiserum was considerably higher during earlier (<65 h) rather than later time points (FIG. 12). These results are especially significant because the experiment was specifically designed to minimize the likelihood of demonstrating protection since (i) the rabbit antibody was raised against gel-purified denatured cysteine protease and not native zymogen or active protease forms (ii) in addition to the protease, the challenge strain is known to express pyrogenic exotoxin A (SPEA) and the recently described Streptococcal superantigen, SSA, and (iii) the cysteine protease precursor made by the challenge strain (SPEB1) differs from the protease precursor variant against which the antiserum was raised (SPEB4) at two amino acid positions (Ala⇋Val at position 111 and Ser⇋Gly at position 308; FIG. 13).

EXAMPLE 22
Mouse immunization—intranasal

Intranasal immunization experiments are conducted essentially as described by Bessen and Fischetti (1988). Briefly, outbred Swiss CD1 mice of the same gender, 4 to 5 weeks old at the onset of immunization are used. Groups of 24 mice are immunized intranasally (i.n.) with 0 or 20 to 100 $\mu$g of zymogen, mature, active protease or synthetic peptide. The mice are immunized once each on days 1, 3, and 5 are rested for 3 weeks and boosted i.n. with a single dose of antigen (20 or 40 g). The initial group of 20 immunized are randomized to two subgroups of 10 animals. Each subgroup is challenged with either the cysteine protease source strain (homologous challenge) or a strain expressing a distinct cysteine protease variant (heterologous challenge). Mice are given 10 ul of the bacterial suspension per nostril at 10 days after the cysteine protease boost. The vaccine is delivered i.n to unanesthetized mice (10 ul per nostril) through a model 750 Hamilton syringe equipped with a repeating dispenser and blunt-end needle. Throats are swabbed beginning 24 hours after challenge and at 24- and 48-hour intervals thereafter until day 11. Additional throat cultures are taken on day 15. Throat swabs are cultured on blood agar plates overnight at 37° C. in a $CO_2$ incubator and betahemolytic colonies are counted the following day.

EXAMPLE 23
Bacterial challenge (intranasal)

The initial group of 24 immunized mice is randomized to two subgroups of 12 animals. Each subgroup is then challenged with either the SPEB source strain (homologous challenge) or a strain expressing a distinct SPEB variant (heterologous challenge). Strains used for challenge are selected for resistance to 200 $\mu$g/ml of streptomycin to facilitate recovery after challenge and if necessary are serially passaged by repeated i.p. injections in mice to increase ability to colonize and infect mice. A single stock of each challenge organism expressing SPEB is prepared from an overnight culture, concentrated 10-fold and stored at −80° C. Stocks are diluted 1:500 and grown overnight at 37° C. in BHI broth, diluted 1:20 in fresh growth medium and cultured to an O.D.650 of 0.5. The cells are harvested by centrifugation and suspended in saline to about $2.5 \times 10^5$ CFU/ml. Inasmuch as streptococci strains differ in ability to colonize mice intranasally, a challenge dose is used that reproducibly colonizes greater than 25% of a nonimmune mouse population. Animals are housed six per cage by cohort. Mice are given 10 $\mu$l of the bacterial suspension per nostril at 10 days after the cysteine protease boost. Throats are swabbed beginning 24 hours after challenge and at 24- to 48-hour intervals thereafter until day 11. Additional throat cultures are taken on day 15. Throat swabs are cultured on blood agar plates with 200 $\mu$g/ml of streptomycin, cultured overnight at 37° C. in a $CO_2$ incubator and beta-hemolytic colonies are counted the following day.

EXAMPLE 24
Immunization of mice—subcutaneous

Immunization experiments are conducted in 4 to 5 week old outbred, immunocompetent, hairless mice (strain Crl-:SKH1 (hrhr)Br; Charles River) of the same gender. These mice are used because lesion size and character is easily cored and animals do not need to be shaved. Groups of 24 mice are immunized subcutaneously (s.c.) with 0, 20, or 40 $\mu$g of zymogen or mature, active protease. The mice are immunized once each on days 1, 7, 14, and 21, rested for 3 weeks and boosted with a single dose of protease (20 or 50 $\mu$g). The mice are checked for seroconversion by a cysteine protease-specific ELISA.

EXAMPLE 25
Bacterial challenge—subcutaneous

Immunized mice are randomized to two groups of 12 animals. Each group is then challenged with either the cysteine protease source strain (homologous challenge) or a strain expressing a distinct cysteine protease variant (heterologous challenge). A single stock of each challenge organism expressing cysteine protease is prepared from an overnight culture and adjusted to $10^6$ CFU/ml. Mice (housed six per cage by cohort) are given 100 $\mu$L of the bacterial suspension mixed with an equal volume of sterile detran beads. The animals are inoculated s.c. on the right flank with a tuberculin syringe. Bacterial dilutions are prepared at the time of challenge to determine the exact number of CFU used. Negative control animals consist of a group of 12 mice sham immunizations. These mice are "challenged" with only sterile medium plus dextran beads.

EXAMPLE 26
Immunological assays

Saliva and serum are collected from all immunized and control mice. Whole saliva is collected by pilocarpine stimulation 920 $\mu$g/mouse, subcutaneous) and centrifuged at 15,000× g for 20 minutes. The material is divided and protease inhibitors are added to one of the aliquots. Storage is at −80° C. Serum is collected by bleeding from the tail vein. Individual and pooled saliva and serum from mice assigned to each cohort, and control mice, are assayed for specific antibody to cysteine protease by ELISA.

EXAMPLE 27
Data analysis

Animals are weighed immediately prior to challenge and every 24 hours post-challenge. Abscess volumes and area of dermo-necrosis will be calculated, and a lesion-size curve determined. Mean lesion sizes are compared statistically between groups by analysis of variance (ANOVA).

EXAMPLE 28
Active immunization of mice

Figure 14:
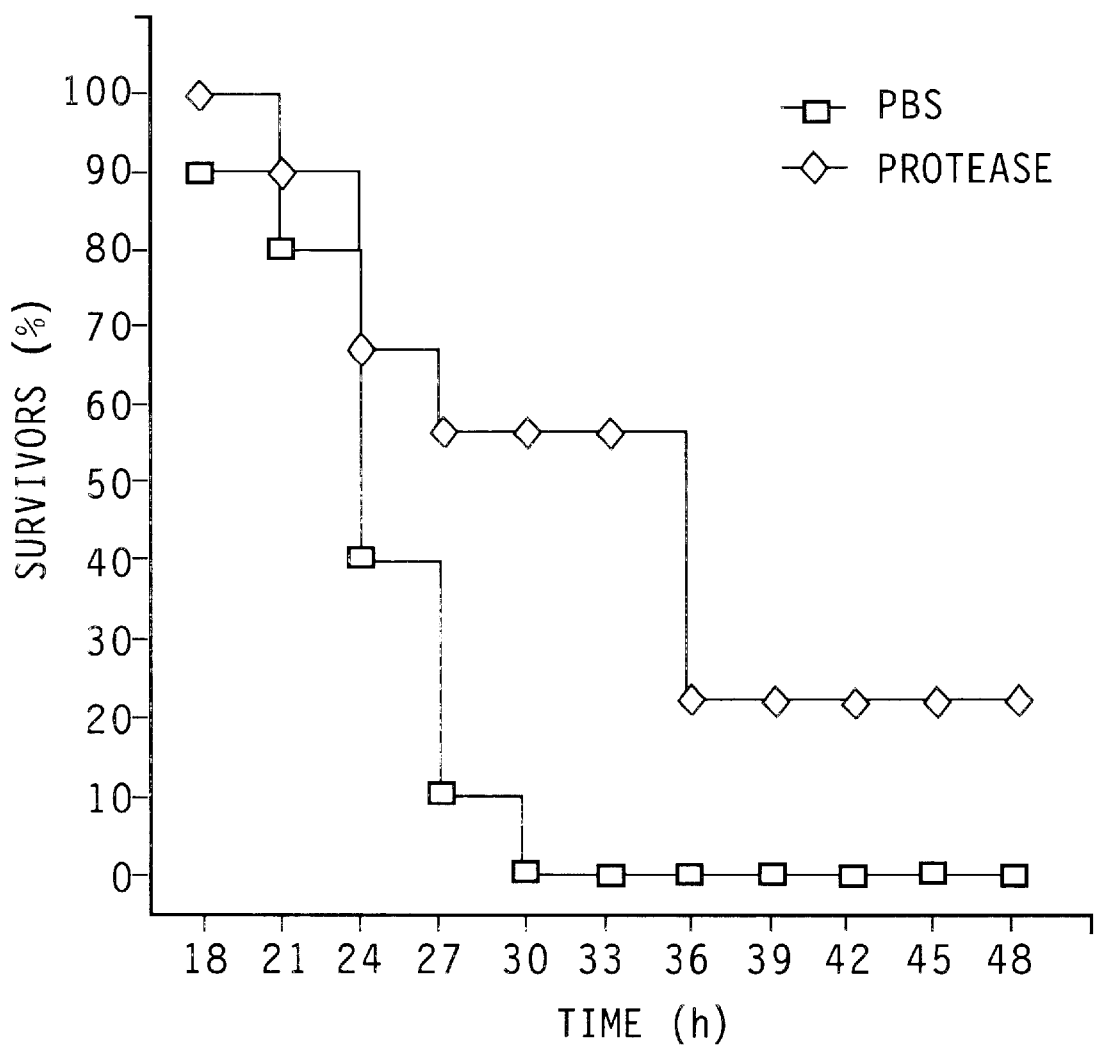
FIG. 14 shows the results of active immunization of mice with the Streptococcal cysteine protease which protects against lethal challenge with heterologous *S. pyogenes*. The data show that intraperitoneal immunization with purified Streptococcal cysteine protease conferred significant protection (log rank test $X^2$; P<0.01) against lethal challenge with the highly virulent *S. pyogenes* isolate MGAS 315.
Figure 15:
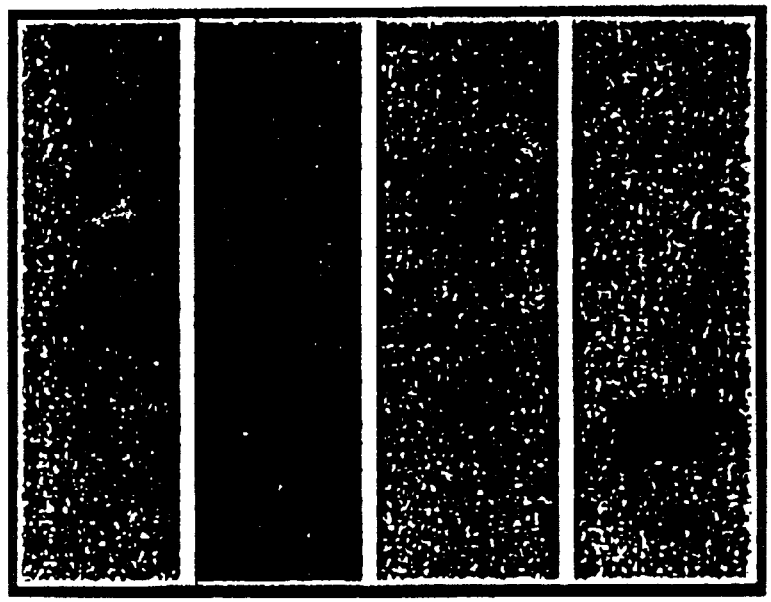
FIG. 15 shows that rabbit serum to streptococcal M3 protein (lane 1), T8 protein (lane 2), or purified IgG from preimmune rabbits (lane 3), does not react with the Streptococcal protease. In contrast, purified IgG from rabbits immunized with the protease reacts specifically with the $M_r$~30 kDa streptococcal extracellular cysteine protease used in active immunization experiments (lane 4).

Male Swiss CD1 outbred mice were inoculated with either PBS (n=9) subcutaneously on day 1, followed with intraperitoneal inoculations of the same treatments at days 7, 14, 21, 42, 50 57, 63, and 79 for a total of nine immunizations. Serum antibody levels to the cysteine protease were checked at days 29, 71, and 84 by ELISA, and the mice were challenged with strain MGAS 315 on day 93, two weeks after the last immunization. The mice were monitored at 3 h intervals, mortality recorded, and Kaplan-Meier survival curves plotted and analyzed as described above. The results (FIG. 14) show that interperitoneal immunization with purified streptococcal cysteine protease also conferred significant protection (log rank test; $X^2$; P<0.01) against lethal challenge with the highly virulent *S. pyogenes* isolate MGAS 315. It is noteworthy that immunization with the cysteine protease also conferred significant protection against *S. pyogenes*-induced early mortality in mice. For example, all 10 mice in the control group were dead by 28 h post challenge, but only 4 of 9 mice died in the protease immunized group (difference in proportions; z; p<0.003). Moreover, at the termination the experiment at 120 h, 2 of 9 mice in the protease-treated but none of 10 mice in the control group survived (difference in proportions; z; P<0.059). Thus, similar to the result observed with mice given immune rabbit serum, active immunization with the streptococcal cysteine protease conferred significant protection against lethal Group A Streptococcal infection.

EXAMPLE 29
PCR Assay for *S. pyogenes*

Genomic DNA was prepared from isolates grown on brain heart infusion agar plates. In general, cells were scraped from one plate, suspended in 800 µl of 10 mM Tris-50 mM EDTA (ph 8.0) (TE), heated at 65° C. for 15 min, washed, resuspended in 500 µl of TE containing 5 µg of mutanolysin, and incubated at 37° C. for 2 h. The cells were lysed by adding 100 µl of 10% sodium dodecyl sulfate and heating at 65° C. for 20 min. After centrifugation for 10 min, the supernatant was transferred to a clean tube and incubated overnight at 37° C. with 100 µg of RNase and 50 µg of proteinase K. The DNA was then extracted with phenol-chloroform, precipitated with ethanol, and suspended in 100 µl of TE.

The cysteine protease structural gene was amplified by the polymerase chain reaction (PCR), with synthetic oligonucleotides. The oligonucleotide primers used to amplify speB and flanking regions were as follows:

SPEB-X (SEQ ID NO:9),
5'-GTTGTCAGTGTCAACTAACCGT-3' and
SPEB-2 (SEQ ID NO:10),
5'-ATCTGTGTCTGATGGATAGCTT-3'.

PCR amplification of 1 µL of chromosomal DNA was performed in 100 µl of a mixture containing 50 mM KCl, 10 mM Tris-HCl, pH 8.3 1.5 mM $MgCl_2$, 0.001% gelatin, 200 µM each of DATP, dCTP, dGTP, and dTTP, 200 nM each of SPEB-X and SPEB-2, and 2.5 units of AmpliTaq DNA polymerase. The thermocycling parameters were denaturation at 94° C. for 1 min. annealing at 55° C. for 2 min, and extension at 72° C. for 2.5 min for a total of 30 cyles. A final extension at 72° C. for 15 min was used.

As shown above, cysteine protease and nucleic acid encoding it can be used as the basis of methods and compositions for detecting Streptococcus, for making antibodies, and for generating a protective immune response in a host mammal.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

---

What is claimed is:

1. A method for determining the presence of a Group A Streptococcus which expresses an extracellular protease capable of degrading proteins of the extracellular matrix, said method comprising:

combining a sample with an assay medium comprising a first member of a specific binding pair which binds to a second member of said specific binding pair in said sample to form a specific binding pair complex, wherein said first member is a protein having one or more epitopic sites immunology competitive with one or more conserved epitopic sites on said extracellular protease, or said first member is an antibody to one or more conserved epitopic sites said extracellular protease; and detecting complex formation as indicative of the presence of said pathogenic organism.

2. The method according to claim 1, wherein said first member is an antiprotease antibody.

3. The method according to claim 2, wherein said protein composition is an antiprotease antibody.

4. The method according to claim 1, wherein said extracellular protease is encoded by an speB gene.

5. The method according to claim 1, wherein said Group A Streptococcus is *Streptococcus pyogenes*.

6. The method according to claim 1, wherein said sample is a physiological fluid.

7. The method according to claim 6, wherein said physiological fluid is serum, plasma, cerebrospinal fluid, or blood.

8. The method according to claim 6, wherein said physiological fluid is a human physiological fluid.

9. The method according to claim 1, wherein said first member is bound to a solid surface.

10. The method according to claim 1, wherein said conserved epitopic site on said extracellular protease is defined as comprising short stretches of at least 10 amino acids in the vicinity of amino acid residues 308–317.

11. The method according to claim 10, wherein the conserved epitopic site on said extracellular protease is defined as comprising short stretches of at least 10 amino acids immediately to the left of amino acid residue 308.

12. The method according to claim 10, wherein the conserved epitopic site on said extracellular protease is defined as comprising short stretches of at least 10 amino acids immediately to the right of amino acid residue 317.

* * * * *

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
      (A) ORGANISM: Streptococcus pyogenes

```
    (viii) POSITION IN GENOME:
          (B) MAP POSITION: 171

(xi) SEQUENCE DESCRIPTION: SEQ ID NO:1:

Pro Val Ile Glu Lys Val Lys Pro Gly Glu Gln Ser Phe Val Gly Gln
1               5                   10                  15

(2) INFORMATION FOR SEQ ID NO:2:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
         (A) ORGANISM: Streptococcus pyogenes (viii) POSITION IN GENOME:
         (B) MAP POSITION: 203

(xi) SEQUENCE DESCRIPTION: SEQ ID NO:2:

Tyr His Asn Tyr Pro Asn Lys Gly Leu Lys Asp Tyr Thr Tyr Thr Leu
1               5                   10                  15

(2) INFORMATION FOR SEQ ID NO:3:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
         (A) ORGANISM: Streptococcus pyogenes (viii) POSITION IN GENOME:
         (B) MAP POSITION: 247

(xi) SEQUENCE DESCRIPTION: SEQ ID NO:3:

Pro Thr Tyr Ser Gly Arg Glu Ser Asn Val Gln Lys Met Ala Ile
1               5                   10                  15

(2) INFORMATION FOR SEQ ID NO:4:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO
```

```
        (v) FRAGMENT TYPE: internal (vi) ORIGINAL SOURCE:
            (A) ORGANISM: Streptococcus pyogenes (viii) POSITION IN GENOME:
            (B) MAP POSITION: 344

(xi) SEQUENCE DESCRIPTION: SEQ ID NO:4:

Ile Asp Gly Ala Asp Gly Arg Asn Phe Tyr His
1               5                   10

(2) INFORMATION FOR SEQ ID NO:5:

(i) SEQUENCE CHARACTERISTICS:
            (A) LENGTH: 398 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
            (A) ORGANISM: Streptococcus pyogenes
            (B) STRAIN: MGAS 1719

(vii) IMMEDIATE SOURCE:
            (B) CLONE: SPEB7 (cysteine protease)

(x) PUBLICATION INFORMATION:
            (A) AUTHORS: Kapur, V.
                         Topouzis, S.
                         Majesky, M. W.
                         Li, L.- L.
                         Hamrick, M. R.
                         Hamill, R. J.
                         Patti, J. M.
                         Musser, J. M.
            (B) TITLE: A conserved Streptococcus pyogenes
                       extracellular cysteine protease cleaves human
                       fibronectin and degrades vitronectin
            (C) JOURNAL: Microb. Pathog.
            (D) VOLUME: 15
            (F) PAGES: 327-346
            (G) DATE: 1993

(xi) SEQUENCE DESCRIPTION: SEQ ID NO:5:

Met Asn Lys Lys Lys Leu Gly Ile Arg Leu Leu Ser Leu Leu Ala Leu
1               5                   10                  15

Gly Gly Phe Val Leu Ala Asn Pro Val Phe Ala Asp Gln Asn Phe Ala
            20                  25                  30

Arg Asn Glu Lys Glu Ala Lys Asp Ser Ala Ile Thr Phe Ile Gln Lys
        35                  40                  45

Ser Ala Ala Ile Lys Ala Gly Ala Arg Ser Ala Glu Asp Ile Lys Leu
    50                  55                  60

Asp Lys Val Asn Leu Gly Gly Glu Leu Ser Gly Ser Asn Met Tyr Val
65                  70                  75                  80

Tyr Asn Ile Ser Thr Gly Gly Phe Val Ile Val Ser Gly Asp Lys Arg
                85                  90                  95

Ser Pro Glu Ile Leu Gly Tyr Ser Thr Ser Gly Ser Phe Asp Ala Asn
            100                 105                 110

Gly Lys Glu Asn Ile Ala Ser Phe Met Glu Ser Tyr Val Glu Gln Ile
```

```
            115                 120                 125
Lys Glu Asn Lys Lys Leu Asp Thr Thr Tyr Ala Gly Thr Ala Glu Ile
130                 135                 140

Lys Gln Pro Val Val Lys Ser Leu Leu Asp Ser Lys Gly Ile His Tyr
145                 150                 155                 160

Asn Gln Gly Asn Pro Tyr Asn Leu Leu Thr Pro Val Ile Glu Lys Val
                165                 170                 175

Lys Pro Gly Glu Gln Ser Phe Val Gly Gln His Ala Ala Thr Gly Cys
            180                 185                 190

Val Ala Thr Ala Thr Ala Gln Ile Met Lys Tyr His Asn Tyr Pro Asn
        195                 200                 205

Lys Gly Leu Lys Asp Tyr Thr Tyr Thr Leu Ser Ser Asn Asn Pro Tyr
210                 215                 220

Phe Asn His Pro Lys Asn Leu Phe Ala Ala Ile Ser Thr Arg Gln Tyr
225                 230                 235                 240

Asn Trp Asn Asn Ile Leu Pro Thr Tyr Ser Gly Arg Glu Ser Asn Val
                245                 250                 255

Gln Lys Met Ala Ile Ser Glu Leu Met Ala Asp Val Gly Ile Ser Val
            260                 265                 270

Asp Met Asp Tyr Gly Pro Ser Ser Gly Ser Ala Gly Ser Ser Arg Val
        275                 280                 285

Gln Arg Ala Leu Lys Glu Asn Phe Gly Tyr Asn Gln Ser Val His Gln
290                 295                 300

Ile Asn Arg Ser Asp Phe Ser Lys Gln Asp Trp Glu Ala Gln Ile Asp
305                 310                 315                 320

Lys Glu Leu Ser Gln Asn Gln Pro Val Tyr Tyr Gln Gly Val Gly Lys
                325                 330                 335

Val Gly Gly His Ala Phe Val Ile Asp Gly Ala Asp Gly Arg Asn Phe
            340                 345                 350

Tyr His Val Asn Trp Gly Trp Gly Gly Val Ser Asp Gly Phe Phe Arg
        355                 360                 365

Leu Asp Ala Leu Asn Pro Ser Ala Leu Gly Thr Gly Gly Gly Ala Gly
370                 375                 380

Gly Phe Asn Gly Tyr Gln Ser Ala Val Val Gly Ile Lys Pro
385                 390                 395

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (vi) ORIGINAL SOURCE:
        (A) ORGANISM: Streptococcus pyogenes (vii) IMMEDIATE SOURCE:
        (B) CLONE: cysteine protease nucleotide binding domain (xi) SEQUENCE DESCRIPTION: SEQ ID NO:6:

Gly Val Gly Lys Val Gly
```

(2) INFORMATION FOR SEQ ID NO:7:

(i) SEQUENCE CHARACTERISTICS:
        (A) LENGTH: 1197 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Streptococcus pyogenes
        (B) STRAIN: MGAS 1719

(vii) IMMEDIATE SOURCE:
        (B) CLONE: speB7 (cysteine protease)

(xi) SEQUENCE DESCRIPTION: SEQ ID NO:7:

```
ATGAATAAAA AGAAATTAGG TATCAGATTA TTAAGTCTTT TAGCATTAGG TGGATTTGTT      60
CTTGCTAACC CAGTATTTGC CGATCAAAAC TTTGCTCGTA ACGAAAAAGA AGCAAAAGAT     120
AGCGCTATCA CATTTATCCA AAAATCAGCA GCTATCAAAG CAGGTGCACG AAGCGCAGAA     180
GATATTAAGC TTGACAAAGT TAACTTAGGT GGAGAACTTT CTGGCTCTAA TATGTATGTT     240
TACAATATTT CTACTGGAGG ATTTGTTATC GTTTCAGGAG ATAAACGTTC TCCAGAAATT     300
CTAGGATACT CTACCAGCGG ATCATTTGAC GCTAACGGTA AGAAAACAT TGCTTCCTTC      360
ATGGAAAGTT ATGTCGAACA AATCAAAGAA AACAAAAAAT TAGACACTAC TTATGCTGGT     420
ACCGCTGAGA TTAAACAACC AGTTGTTAAA TCTCTCCTTG ATTCAAAAGG CATTCATTAC     480
AACCAAGGTA ACCCTTACAA CCTATTGACA CCTGTTATTG AAAAAGTAAA ACCAGGTGAA     540
CAATCTTTTG TAGGTCAACA TGCAGCTACA GGATGTGTTG CTACTGCAAC TGCTCAAATT     600
ATGAAATATC ATAATTACCC TAACAAAGGG TTGAAAGACT ACACTTAGAC ACTAAGCTCA     660
AATAACCCAT ATTTCAACCA TCCTAAGAAC TTGTTTGCAG CTATCTCTAC TAGACAATAC     720
AACTGGAACA ACATCCTACC TACTTATAGC GGAAGAGAAT CTAACGTTCA AAAAATGGCG     780
ATTTCAGAAT TGATGGCTGA TGTTGGTATT TCAGTAGACA TGGATTATGG TCCATCTAGT     840
GGTTCTGCAG GTAGCTCTCG TGTTCAAAGA GCCTTGAAAG AAAACTTTGG CTACAACCAA     900
TCTGTTCACC AAATTAACCG TAGCGACTTT AGCAAACAAG ATTGGGAAGC ACAAATTGAC     960
AAAGAATTAT CTCAAAACCA ACCAGTATAC TACCAAGGTG TCGGTAAAGT AGGCGGACAT    1020
GCCTTTGTTA TCGATGGTGC TGACGGACGT AACTTCTACC ATGTTAACTG GGGTTGGGGT    1080
GGAGTCTCTG ACGGCTTCTT CCGTCTTGAC GCACTAAACC CTTCAGCTCT TGGTACTGGT    1140
GGCGGCGCAG GCGGCTTCAA CGGTTACCAA AGTGCTGTTG TAGGCACTAA ACCTTAG      1197
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: Streptococcus pyogenes
             (B) STRAIN: MGAS 1719

(vii) IMMEDIATE SOURCE:
             (B) CLONE: cysteine protease (viii) POSITION IN GENOME:
             (B) MAP POSITION: 146-156

(xi) SEQUENCE DESCRIPTION: SEQ ID NO:8:

Gln Pro Val Val Lys Ser Leu Leu Asp Ser Lys
1               5                   10

(2) INFORMATION FOR SEQ ID NO:9:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "Oligonucleotide"

(iii) HYPOTHETICAL: NO (iv) ANTI-SENSE: NO (vi) ORIGINAL SOURCE:
             (A) ORGANISM: Streptococcus pyogenes (vii) IMMEDIATE SOURCE:
             (B) CLONE: SPEB-X (xi) SEQUENCE DESCRIPTION: SEQ ID NO:9:

GTTGTCAGTG TCAACTAACC GT                                                    22

(2) INFORMATION FOR SEQ ID NO:10:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "Oligonucleotide"

(iii) HYPOTHETICAL: NO (iv) ANTI-SENSE: NO (vi) ORIGINAL SOURCE:
             (A) ORGANISM: Streptococcus pyogenes (vii) IMMEDIATE SOURCE:
             (B) CLONE: SPEB-2

(xi) SEQUENCE DESCRIPTION: SEQ ID NO:10:

ATCTGTGTCT GATGGATAGC TT                                                    22

(2) INFORMATION FOR SEQ ID NO:11:

(i) SEQUENCE CHARACTERISTICS:
             (A) LENGTH: 23 base pairs
             (B) TYPE: nucleic acid
             (C) STRANDEDNESS: single
             (D) TOPOLOGY: linear

```
    (ii) MOLECULE TYPE: other nucleic acid
         (A) DESCRIPTION: /desc = "Oligonucleotide"

(iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: SPEB-1

(xi) SEQUENCE DESCRIPTION: SEQ ID NO:11:

CTTTCTGGCT CTAATATGTA TGT                                             23

(2) INFORMATION FOR SEQ ID NO:12:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide"

(iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: SPEB-3

(xi) SEQUENCE DESCRIPTION: SEQ ID NO:12:

GTTATTGAAA AAGTAAAACC                                                 20

(2) INFORMATION FOR SEQ ID NO:13:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide"

(iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: SPEB-4

(xi) SEQUENCE DESCRIPTION: SEQ ID NO:13:

TTTTCAATAA CAGGTGTCAA                                                 20

(2) INFORMATION FOR SEQ ID NO:14:

(i) SEQUENCE CHARACTERISTICS:
         (A) LENGTH: 20 base pairs
         (B) TYPE: nucleic acid
         (C) STRANDEDNESS: single
         (D) TOPOLOGY: linear
```

```
        (ii) MOLECULE TYPE: other nucleic acid
             (A) DESCRIPTION: /desc = "Oligonucleotide"

(iii) HYPOTHETICAL: NO (iv) ANTI-SENSE: NO (vi) ORIGINAL SOURCE:
             (A) ORGANISM: Streptococcus pyogenes (vii) IMMEDIATE SOURCE:
             (B) CLONE: SPEB-Y (xi) SEQUENCE DESCRIPTION: SEQ ID NO:14:

TCTCCTGAAA CGATAACAAA                                                       20

(2) INFORMATION FOR SEQ ID NO:15:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: Streptococcus pyogenes (vii) IMMEDIATE SOURCE:
             (B) CLONE: Peptide 1

(viii) POSITION IN GENOME:
             (B) MAP POSITION: 303

(xi) SEQUENCE DESCRIPTION: SEQ ID NO:15:

His Gln Ile Asn Arg Ser Asp Phe Ser Lys Gln Asp Trp Glu Ala Gln
1               5                   10                  15

Ile Asp Lys Glu
            20

(2) INFORMATION FOR SEQ ID NO:16:

(i) SEQUENCE CHARACTERISTICS:
             (A) LENGTH: 19 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: Streptococcus pyogenes (vii) IMMEDIATE SOURCE:
             (B) CLONE: Peptide 2

(viii) POSITION IN GENOME:
             (B) MAP POSITION: 304

(xi) SEQUENCE DESCRIPTION: SEQ ID NO:16:
```

```
His Gln Ile Asn Gly Asp Phe Ser Lys Gln Asp Trp Glu Ala Gln Ile
1               5                   10                  15

Asp Lys Glu
```

(2) INFORMATION FOR SEQ ID NO:17:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Streptococcus pyogenes (vii) IMMEDIATE SOURCE:
        (B) CLONE: Peptide 3

(viii) POSITION IN GENOME:
        (B) MAP POSITION: 304

(xi) SEQUENCE DESCRIPTION: SEQ ID NO:17:

```
His Gln Ile Asn Ser Asp Phe Ser Lys Gln Asp Trp Glu Ala Gln Ile
1               5                   10                  15

Asp Lys Glu
```

(2) INFORMATION FOR SEQ ID NO:18:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Streptococcus pyogenes (viii) POSITION IN GENOME:
        (B) MAP POSITION: 304

(xi) SEQUENCE DESCRIPTION: SEQ ID NO:18:

```
Gln Ile Asn Arg Ser Asp Phe Ser Lys Gln
1               5                   10
```

(2) INFORMATION FOR SEQ ID NO:19:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: Streptococcus pyogenes (viii) POSITION IN GENOME:
             (B) MAP POSITION: 304

(xi) SEQUENCE DESCRIPTION: SEQ ID NO:19:

Gln Ile Asn Arg Gly Asp Phe Ser Lys Gln
1               5                   10

(2) INFORMATION FOR SEQ ID NO:20:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: speB1

(xi) SEQUENCE DESCRIPTION: SEQ ID NO:20:

ACAGCAAAGT GCCCCCGCCC CTCCCCAATA CGACTACTAC CAGGA         45

(2) INFORMATION FOR SEQ ID NO:21:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: speB2

(xi) SEQUENCE DESCRIPTION: SEQ ID NO:21:

ACAGCAAGGT GCCCCCGCCT CTCTCCAACG CGACTACTAC CAGGA         45

(2) INFORMATION FOR SEQ ID NO:22:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO

```
    (vi) ORIGINAL SOURCE:
         (A) ORGANISM: Streptococcus pyogenes (vii) IMMEDIATE SOURCE:
         (B) CLONE: speB3

(xi) SEQUENCE DESCRIPTION: SEQ ID NO:22:

ACAGCAAAGT GCCCCCGCCT CTCCCCAACA CGACTACTAC CAGGA          45

(2) INFORMATION FOR SEQ ID NO:23:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: speB4

(xi) SEQUENCE DESCRIPTION: SEQ ID NO:23:

ACAGCAAAGT GCTCCCGCCT CTCCCCAACA CTACTACTAC CAGGA          45

(2) INFORMATION FOR SEQ ID NO:24:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: speB5

(xi) SEQUENCE DESCRIPTION: SEQ ID NO:24:

ACAGCAAAGT GCCCCCGCCT CTCCCCAATA CGACTACTAC CAGGA          45

(2) INFORMATION FOR SEQ ID NO:25:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes
```

(vii) IMMEDIATE SOURCE:
             (B) CLONE: speB6

(xi) SEQUENCE DESCRIPTION: SEQ ID NO:25:

ACAGCAAAGT GCCCCCGCCC CTCCCTAACA CGACTACTAC CAGGA         45

(2) INFORMATION FOR SEQ ID NO:26:

(i) SEQUENCE CHARACTERISTICS:
             (A) LENGTH: 45 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Streptococcus pyogenes (vii) IMMEDIATE SOURCE:
             (B) CLONE: speB7

(xi) SEQUENCE DESCRIPTION: SEQ ID NO:26:

ACAGCAAAGT GCTCCCGCCC CTCTCCAACG CGACTACTAT CAGGA         45

(2) INFORMATION FOR SEQ ID NO:27:

(i) SEQUENCE CHARACTERISTICS:
             (A) LENGTH: 45 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Streptococcus pyogenes (vii) IMMEDIATE SOURCE:
             (B) CLONE: speB8

(xi) SEQUENCE DESCRIPTION: SEQ ID NO:27:

ACAGCAAAGT GCTCCCGCCT CTCCCCAACA CGACTACTAC CAGGA         45

(2) INFORMATION FOR SEQ ID NO:28:

(i) SEQUENCE CHARACTERISTICS:
             (A) LENGTH: 45 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Streptococcus pyogenes (vii) IMMEDIATE SOURCE:
             (B) CLONE: speB9

(xi) SEQUENCE DESCRIPTION: SEQ ID NO:28:

ACGGCAAAGT GCCCCCGCCT CTCCCCAACA CGACTACTAC CAGGA          45

(2) INFORMATION FOR SEQ ID NO:29:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB10

(xi) SEQUENCE DESCRIPTION: SEQ ID NO:29:

ACAGCAAAGC GCCCCCGCCT CTCCCCAACA CGACCACTAC CAGGA          45

(2) INFORMATION FOR SEQ ID NO:30:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB11

(xi) SEQUENCE DESCRIPTION: SEQ ID NO:30:

ACGGTAAAGT GCCCTCGCCC CTCCCCAACA TTACTACTAC CAGGA          45

(2) INFORMATION FOR SEQ ID NO:31:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB12

(xi) SEQUENCE DESCRIPTION: SEQ ID NO:31:

ACAACAAAGT GCCCCCACCC CTCCCCAATA CGACTACTAC CAGGA          45

(2) INFORMATION FOR SEQ ID NO:32:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB13

(xi) SEQUENCE DESCRIPTION: SEQ ID NO:32:

ACAGCAAAGT GCCCCCGCCT CGCCCCAACA CGACTACTAC CAGAA                45

(2) INFORMATION FOR SEQ ID NO:33:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB14

(xi) SEQUENCE DESCRIPTION: SEQ ID NO:33:

ACAGCAAAGT GCCCCCGCCC CTCCCCAACA CGACTACTAC CAGGA                45

(2) INFORMATION FOR SEQ ID NO:34:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB15

(xi) SEQUENCE DESCRIPTION: SEQ ID NO:34:

ACAGCAAAGT GCCCCCGCCT CTCCCCAACG CGACTACTCC CAGGA                45

(2) INFORMATION FOR SEQ ID NO:35:

(i) SEQUENCE CHARACTERISTICS:
        (A) LENGTH: 45 base pairs

```
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Streptococcus pyogenes (vii) IMMEDIATE SOURCE:
            (B) CLONE: speB16

(xi) SEQUENCE DESCRIPTION: SEQ ID NO:35:

ACAGCAAAGT GCCCCCGCCT CGCCCCAACA CGACTACTAC CAGGA                    45

(2) INFORMATION FOR SEQ ID NO:36:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Streptococcus pyogenes (vii) IMMEDIATE SOURCE:
            (B) CLONE: speB17

(xi) SEQUENCE DESCRIPTION: SEQ ID NO:36:

ACAGCAAAGT GCCCCCGCCC CTCCCCAACA CTACTACTAC CAGGA                    45

(2) INFORMATION FOR SEQ ID NO:37:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Streptococcus pyogenes (vii) IMMEDIATE SOURCE:
            (B) CLONE: speB18

(xi) SEQUENCE DESCRIPTION: SEQ ID NO:37:

ACGGTAAAGT GCCCTCGCCT CTCCCCCACA TTACTACTAC CAGGA                    45

(2) INFORMATION FOR SEQ ID NO:38:

(i) SEQUENCE CHARACTERISTICS:
            (A) LENGTH: 45 base pairs
            (B) TYPE: nucleic acid
            (C) STRANDEDNESS: single
            (D) TOPOLOGY: linear
```

(ii) MOLECULE TYPE: DNA (genomic)

(iii) HYPOTHETICAL: NO (iv) ANTI-SENSE: NO (vi) ORIGINAL SOURCE:
             (A) ORGANISM: Streptococcus pyogenes (vii) IMMEDIATE SOURCE:
             (B) CLONE: speB19

(xi) SEQUENCE DESCRIPTION: SEQ ID NO:38:

ACAGCAAAGT GTTCCCGCCC TTCCCCAACA TGACTACTAC TAGGA         45

(2) INFORMATION FOR SEQ ID NO:39:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Streptococcus pyogenes (vii) IMMEDIATE SOURCE:
             (B) CLONE: speB20

(xi) SEQUENCE DESCRIPTION: SEQ ID NO:39:

ACAGCAAAGT GCTCCCGCCC TTCTCCAACA CGACCACTAC CAGGC         45

(2) INFORMATION FOR SEQ ID NO:40:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Streptococcus pyogenes (vii) IMMEDIATE SOURCE:
             (B) CLONE: speB21

(xi) SEQUENCE DESCRIPTION: SEQ ID NO:40:

ACAGCAAAGT GCCCCCGTCC CTCCCCAACA CTACTACTAC CAGGA         45

(2) INFORMATION FOR SEQ ID NO:41:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Streptococcus pyogenes (vii) IMMEDIATE SOURCE:
            (B) CLONE: speB22

(xi) SEQUENCE DESCRIPTION: SEQ ID NO:41:

ACAGCAAAGT GCCCCCGCCC CTCCCCAACG CGACTACTAC CAGGA          45

(2) INFORMATION FOR SEQ ID NO:42:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Streptococcus pyogenes (vii) IMMEDIATE SOURCE:
            (B) CLONE: speB23

(xi) SEQUENCE DESCRIPTION: SEQ ID NO:42:

ACGGCAAAGT GCCCCTGCCT CTCCCCAACA CGGCTACTAC CAGGA          45

(2) INFORMATION FOR SEQ ID NO:43:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Streptococcus pyogenes (vii) IMMEDIATE SOURCE:
            (B) CLONE: speB24

(xi) SEQUENCE DESCRIPTION: SEQ ID NO:43:

ATAGCAAAGT GCTCCCGCCC TTCTCCAACG CGACTACTAC CAGGA          45

(2) INFORMATION FOR SEQ ID NO:44:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Streptococcus pyogenes

```
   (vii) IMMEDIATE SOURCE:
         (B) CLONE: speB25

(xi) SEQUENCE DESCRIPTION: SEQ ID NO:44:

GCAGCAAAGT ACTCCCGCCC CTCCCCAACA TTACTACCAC CAGGA                    45

(2) INFORMATION FOR SEQ ID NO:45:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: speB26

(xi) SEQUENCE DESCRIPTION: SEQ ID NO:45:

ACAGCAAAGT GCCCCCGCCT CGCCCCAACA CGACTATTAC CGGGA                    45

(2) INFORMATION FOR SEQ ID NO:46:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: speB27

(xi) SEQUENCE DESCRIPTION: SEQ ID NO:46:

ACAGCAAAGT GCCCCCGCCC CTCCTCAATA CGACTACTAC CAGGA                    45

(2) INFORMATION FOR SEQ ID NO:47:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: speB28
```

(xi) SEQUENCE DESCRIPTION: SEQ ID NO:47:

ACAGCGAAGT GCCCCCGCCT CTCCCCAACA CGACTACTAC CAGGA                45

(2) INFORMATION FOR SEQ ID NO:48:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB29

(xi) SEQUENCE DESCRIPTION: SEQ ID NO:48:

ACAGCAAGTG CCCCCGCCTT TCCCCAACAT GACTACTACC AGGA                 44

(2) INFORMATION FOR SEQ ID NO:49:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB30

(xi) SEQUENCE DESCRIPTION: SEQ ID NO:49:

ACAGCAAAGT GCTCCCGCCC CTCTCCAACA CGACTACTAC CAGGA                45

(2) INFORMATION FOR SEQ ID NO:50:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB31

(xi) SEQUENCE DESCRIPTION: SEQ ID NO:50:

ACGGCAAAGT GCCCTCGCCT CTCCCCAACA TGACTACTAC CAGGA                45

(2) INFORMATION FOR SEQ ID NO:51:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB32

(xi) SEQUENCE DESCRIPTION: SEQ ID NO:51:

ACAGCAAAGT GCCCCCGCCT TTCCCCAACA TTACTACTAC CAGGA          45

(2) INFORMATION FOR SEQ ID NO:52:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB33

(xi) SEQUENCE DESCRIPTION: SEQ ID NO:52:

ACAGCAAAGT GCCCCCGCCT CTCTCCAACG CGACTACTAC CAGGA          45

(2) INFORMATION FOR SEQ ID NO:53:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB34

(xi) SEQUENCE DESCRIPTION: SEQ ID NO:53:

ACAGCAAAGT GCCCCCGCCT TTCCCCAACG CGACTACTCC CAAGA          45

(2) INFORMATION FOR SEQ ID NO:54:

(i) SEQUENCE CHARACTERISTICS:

```
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes (vii) IMMEDIATE SOURCE:
         (B) CLONE: speB35

(xi) SEQUENCE DESCRIPTION: SEQ ID NO:54:

ACAGCAAAGT GCCCCCGCCC CTCCCCAGTA CGATTACTAT CAGGA                     45

(2) INFORMATION FOR SEQ ID NO:55:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB36

(xi) SEQUENCE DESCRIPTION: SEQ ID NO:55:

ACAGCAAAGT GCCCCCGCCT CTTTCCAACG CGACTACTAC CAGGA                     45

(2) INFORMATION FOR SEQ ID NO:56:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (vii) IMMEDIATE SOURCE:
        (B) CLONE: speB37

(xi) SEQUENCE DESCRIPTION: SEQ ID NO:56:

ACAGCAAAGT GCTCCCGCTC CTCTCCAACA CGACTACTAC CAGGA                     45

(2) INFORMATION FOR SEQ ID NO:57:

(i) SEQUENCE CHARACTERISTICS:
        (A) LENGTH: 45 base pairs
        (B) TYPE: nucleic acid
        (C) STRANDEDNESS: single
        (D) TOPOLOGY: linear
```

```
      (ii) MOLECULE TYPE: DNA (genomic)

(iii) HYPOTHETICAL: NO (iv) ANTI-SENSE: NO (vi) ORIGINAL SOURCE:
           (A) ORGANISM: Streptococcus pyogenes (vii) IMMEDIATE SOURCE:
           (B) CLONE: speB38

(xi) SEQUENCE DESCRIPTION: SEQ ID NO:57:

ACAGCAAAGT GCCTCCGCCT CTCTCCAACG CGACTACTAC CAGGA                              45

(2) INFORMATION FOR SEQ ID NO:58:

(i) SEQUENCE CHARACTERISTICS:
          (A) LENGTH: 45 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Streptococcus pyogenes (vii) IMMEDIATE SOURCE:
          (B) CLONE: speB39

(xi) SEQUENCE DESCRIPTION: SEQ ID NO:58:

ACAGCAAAAT GCCCCCGCCC CTCTCCAACA CGACTACTAC CAGGA                              45
```